(12) United States Patent
Henegar et al.

(10) Patent No.: US 6,444,820 B1
(45) Date of Patent: Sep. 3, 2002

(54) PROCESS FOR THE MANUFACTURE OF CAMPTOTHECIN DERIVATIVES

(76) Inventors: Kevin E. Henegar, 6136 Sablewood Cir., Portage, MI (US) 49024; John C. Sih, 3721 Greenleaf Cir., Kalamazoo, MI (US) 49008

( * ) Notice: Subject to any disclaimer, the term of this patent is extended or adjusted under 35 U.S.C. 154(b) by 0 days.

(21) Appl. No.: 09/687,227

(22) Filed: Oct. 13, 2000

Related U.S. Application Data

(60) Division of application No. 09/511,006, filed on Feb. 22, 2000, now Pat. No. 6,235,907, which is a division of application No. 09/230,245, filed as application No. PCT/US96/04163 on Apr. 1, 1996, now Pat. No. 6,121,451, which is a continuation-in-part of application No. 08/419,643, filed on Apr. 7, 1995, now abandoned.

(51) Int. Cl.[7] .................... C07D 491/22; C07D 491/147
(52) U.S. Cl. .......................................... 546/48; 546/92
(58) Field of Search ...................... 546/48, 92

(56) References Cited

U.S. PATENT DOCUMENTS

| 4,778,891 | A |   | 10/1988 | Tagawa et al. ............... 546/18 |
| 4,894,456 | A |   | 1/1990  | Wall et al. .................... 546/41 |
| 5,053,512 | A |   | 10/1991 | Wani et al. ................... 546/41 |
| 5,405,963 | A | * | 4/1995  | Fortunak et al. ............. 546/48 |

FOREIGN PATENT DOCUMENTS

| EP | 0 220 601    | 10/1986 | ......... C07D/491/14 |
| WO | 90/03169     | 4/1990  | .......... A61K/31/47 |
| WO | WO 94/29310  | 12/1994 | |

OTHER PUBLICATIONS

M. Shamma, D.A. Smithers, V. St. George, Tetrahedron, 1973, 1949–1954.
H. Terasawa, M. Sugimori, A. Ejima, H. Tagawa, Chem. Pharm. Bull., 1989, 37, 3382–3385.
A. Ejima, H. Terasawa, M. Sugimori, H. Tagawa, J.C.S. Perkin I, 1990, 27–31.
M.C. Wani, A.W. Nicholas, M.E. Wall J. Med. Chem. 1987, 2317–2319.

\* cited by examiner

*Primary Examiner*—Bernard Dentz

(57) ABSTRACT

This invention discloses and claims novel intermediates and procedures for the synthesis of camptothecin derivatives, such as irinotecan, and other compounds related to the synthesis of CPT-11. Related procedures and compounds are also disclosed, such as a novel method of making mappicine.

9 Claims, No Drawings

PROCESS FOR THE MANUFACTURE OF CAMPTOTHECIN DERIVATIVES

This application is a divisional of U.S. application Ser. No. 09/511,006, filed Feb. 22, 2000, now U.S. Pat. No. 6,235,907 which is a divisional of U.S. application Ser. No. 09/230,245, filed Oct. 2, 1997, now U.S. Pat. No. 6,121,451 which is the national phase of International Application No. PCT/US96/04163, International Filing Date Apr. 1, 1996, now U.S. Pat. No. 6,121,451, which is a continuation-in-part of U.S. application Ser. No. 08/419,643, filed Apr. 7, 1995, now abandoned.

FIELD OF THE INVENTION

This invention discloses and claims novel intermediates and procedures for the synthesis of camptothecin derivatives, such as irinotecan, and other compounds related to the synthesis of CPT- 11. Related procedures and compounds are also disclosed, such as a novel method of making mappicine.

INFORMATION DISCLOSURE

The compound given the label 14CPT in this document is mentioned in M. Shamma, D. A. Smithers, V. St. George, Tetrahedron, 1973, 1949–1954.

The asymmetric synthesis of this compound, 14 CPT, is reported in the following documents (grouped by author):
Group 1.
  H. Terasawa, M. Sugimori, A. Ejima, H. Tagawa, Chem. Pharm. Bull., 1989, 37, 3382–3385.
  A. Ejima, H. Terasawa, M. Sugimori, H. Tagawa, J. C. S. Perkin I, 1990, 27–31.
  H. Tagawa, H. Terasawa, A. Ejima, U.S. Pat. No. 4,778,891 (Oct. 18, 1988).
  H. Tagawa, H. Terasawa, A. Ejima, E P 220601 (Oct 14, 1986).
Group 2.
  M. C. Wani, A. W. Nicholas, M. E. Wall, J. Med. Chem. 1987, 2317–2319.
  M. C. Wani, A. W. Nicholas, M. E. Wall, U.S. Pat. No. 5,053,512 (Oct 1, 1990).
  M. E. Wall, M. C. Wani, A. W. Nicholas, G. Manikumar, U.S. Pat. No. 4,894,456 (Jan. 16, 1990).
  M. E Wall, M. C. Wani, A. W. Nicholas, and G. Manikumar, WO 90/03169 (Sep. 28, 1988).

Background

Camptothecin derivatives, such as irinotecan, are effective anticancer drugs. This invention describes an efficient method of synthetic synthesis for a variety of camptothecin derivatives, including irinotecan or CPT-11, and other useful compounds like mappicine.

SUMMARY OF THE INVENTION

This invention comprises compounds, processes, reactions and reagents as shown in the CHARTS, formulas and figures herein. The compounds, processes, reactions and reagents are useful for the manufacture of camptothecin derivatives such as CPT-11 and other related compounds such as mappicine.

Specific compounds selected from the compounds described and labeled in the specification are the compounds in the CHARTS labeled 2G, 3G, 4G, 5G, 6G, 7GG, 7GA, 8GG, 8GA, 8GB, 9GG, 9GA, 10G, 10G(S), 10G(R), 11G, 11G(S), 11G(R), 12GA-1, 12GA-1(S), 12GA-1(R), 12GA-2, 12GA-2(S), 12GA-2(R), 12GB-1, 12GB-1(S), 12GB-1(R), 12GB-2, 12GB-2(S), 12GB-2(R), 12G, 12G(S), 12G(R), 13G, 13G(S), or 13G(R), where $R_1$ is any optionally substituted $C_{1-8}$ alkyl, including lower alkyl, $C_{3-10}$ cycloalkyl, lower alkyl-$C_{3-10}$ cycloalkyl, alkenyl, aryl, substituted aryl, alkylaryl, or substituted alkylaryl, including benzyl and substituted benzyl;

where $R_2$ is H,
  a) any optionally substituted alkyl, including $C_{1-8}$alkyl, alkylaryl, including $C_{1-6}$alkyl-aryl, $C_{1-8}$alkyl-$C_6$aryl, substituted benzyl and unsubstituted benzyl;
  b) —C(O)—$R_3$, or
  c) —C($R_7$)$_2$—O—$R_3$ where each $R_7$ is independent of the other;

where $R_3$ is H, optionally substituted $C_{1-8}$ alkyl, including lower alkyl, cycloalkyl, alkenyl, aryl, substituted aryl, and alkylaryl, or substituted alkylaryl, including benzyl and substituted benzyl;

where $R_4$ is H, optionally substituted $C_{1-8}$ alkyl, including lower alkyl, $C_{3-10}$ cycloalkyl, lower alkyl-$C_{3-10}$ cycloalkyl, alkenyl, aryl, substituted aryl, alkylaryl, or substituted alkylaryl, including benzyl and substituted benzyl;

where $R_5$ is H, optionally substituted $C_{1-8}$ alkyl, including lower alkyl, aryl, substituted aryl, or two $R_5$ groups may be combined to form cyclopentane or cyclohexane, or substituted derivatives thereof;

where $R_6$ is optionally substituted $C_{1-8}$ alkyl, lower alkyl, including ethyl, aryl, substituted aryl, alkylaryl, substituted alkylaryl, including benzyl and substituted benzyl, $C_{3-10}$ cycloalkyl, lower alkyl-$C_{3-10}$ cycloalkyl, heteroaryl, or substituted heteroaryl, where $R_7$ is independently H, optionally substituted $C_{1-8}$ alkyl, including lower alkyl, aryl, substituted aryl, alkylaryl, substituted alkylaryl, or two $R_7$ groups may be combined to form cyclopentane or cyclohexane or substituted derivatives thereof.

where $R_8$ is optionally substituted $C_{1-6}$ alkyl, including lower alkyl, including t-butyl, $C_{3-10}$ cycloalkyl, lower alkyl-$C_{3-10}$ cycloalkyl, alkenyl, aryl, substituted aryl, alkylaryl, or substituted alkylaryl, including benzyl and substituted benzyl.

Other specific compounds of the invention are selected from the compounds described and labeled in the specification are 2CPT, 3CPT, 4CPT, 5CPT, 6CPT, 7CPT, 7CPTA, 8CPTG, 8CPTA, 8CPTAB, 9CPTG, 9CPTA, 9CPTB, 10CPT, 10CPT(S), 10CPT(R), 11CPT, 11CPT(S), 11CPT(R), 12CPTA-1, 12CPTA-1(S), 12CPTA-1(R), 12CPTA-2, 12CPTA-2(S), 12CPTA-2(R), 12CPTB-1, 12CPTB-1(S), 12CPTB-1(R), 12CPTB-2, 12CPTB-2(S), 12CPTB-2(R), 12CPT, 12CPT(S), 12CPT(R), 13CPT, 13CPT(S), and 13CPT(R) where $R_1$–$R_9$ is defined above.

Other specific compounds of the invention are selected from the compounds described and labeled in the specification as 6MG, 7MG, 8MG, 9MG, 10MG, 11MG,12MG, 13MG, except where 13MG has an $R_6$ that is $C_{1-2}$ alkyl, where the variables have the same definition as the variables above.

Other specific compounds of the invention are selected from the compounds described and labeled in the specification as 5MM, 6MM, 7MM, 8MM, 9MM, 10MM, 11MM, or 12MM.

In addition to the compounds, various procedures labeled as STEPS are also described and claimed in this invention. Those STEPS include the STEPS described and labeled in the specification as CHART G comprising; STEP 2, or STEP 3, or STEP 4, or STEP 5, or STEP 5a, or STEP 5b, or STEP 6, or STEP 7GG, or STEP 7GA, or STEP 8GG, or STEP 8GA, or STEP 8GB, or STEP 9GG, or STEP 9GA, or STEP 9GB, or STEP 10GG, or STEP 10GA, or STEP 10 Resolution, or STEP 11, or STEPS 12, or STEP 13, or STEP 14 or any combination thereof combining two or more STEPS.

Also described and claimed are those STEPS described and labeled in the specification as CHART CPT comprising; STEP 7G, or STEP 7A, or STEP 8G, or STEP 8A, or STEP 8B, or STEP 9G, or STEP 9A, or STEP 9B, or STEP 10G, or STEP 10A, or STEP 11, or STEP 12, or STEP 13, or STEP 14 or any combination thereof combining two or more STEPS.

Also described and claimed are those STEPS described and labeled in the specification as CHART M-G comprising; STEP 5, or STEP 6, or STEP 7, or STEP 8 or STEP 9, or STEP 10, or STEP 11, or STEP 12, or STEP 13, or any combination thereof combining two or more STEPS.

Also described and claimed are those STEPS described and labeled in the specification as CHART M-M comprising; STEP 5, or STEP 6, or STEP 7, or STEP 8 or STEP 9, or STEP 10, or STEP 11, or STEP 12, or STEP 13, or any combination thereof combining two or more STEPS.

Additional Description of the Invention and Description of the Preferred Embodiment(s)

DETAILED DESCRIPTION OF THE INVENTION

The compounds of this invention are identified in two ways: by descriptive names and by reference to structures indicating various chemical entities. In appropriate situations, the proper stereochemistry is also described either with writing or represented in the structures. In some cases, when a molecule has two chiral centers, only the stereochemistry of one chiral center is indicated, unless the stereochemistry of the other chiral center is taught, the stereochemistry of the other chiral chiral center is unresolved or racemic. All the temperatures provided are in degrees centigrade, whether indicated with "°" or "C°" or not. Minute may be written m or min. Hour may be written H or h. Abbreviations are standard or obvious to a chemist unless indicated otherwise. When compounds are added or exposed in any fashion to other compounds they may be said to be "mixed" with those compounds. Usually the purpose in mixing compounds is to promote chemical reactions among one or more of the mixed compounds. The following terms may also be used.

OPTIONALLY SUBSTITUTED

The term "substituted" or "optionally substituted" usually appears first before "$C_{1-8}$alkyl" but should be understood to modify all variations of all r groups. The term shall mean a group or radical that is substituted with halogen, lower alkyl, mono- or di(lower alkyl)-substituted lower alkyl, (lower alkyl)thio, halo-substituted lower alkyl, amino-substituted lower alkyl, mono- or di(lower alkyl)-substituted amino, lower alkenyl, lower alkynyl, halogen, lower alkoxy, aryloxy, aryl(lower alkyl), hydroxy, cyano, amino, mono- and di(lower alkyl)amino, or nitro and the like. A chemist ordinarily skilled in the art would know when and how to make such obvious substitutions.

ALKYL

The parenthetical term ($C_n$–$C_m$ alkyl) is inclusive such that a compound of ($C_1$–$C_8$) would include compounds of 1 to 8 carbons and their isomeric forms. The various carbon moieties are aliphatic hydrocarbon radicals and includes branched or unbranched forms such as methyl, ethyl, n-propyl, isopropyl, n-butyl, isobutyl, sec-butyl, t-butyl, n-pentyl, isopentyl, n-hexyl, isohexyl, n-heptyl, isoheptyl, and n-octyl and isomeric forms thereof.

n-ALKYL

The parenthetical term ($C_n$–$C_m$ n-alkyl) is inclusive such that a compound of ($C_1$–$C_8$) would include compounds of 1 to 8 carbons in their straight chain unbranched form.

LOWER ALKYL

The term "lower alkyl" refers to branched or unbranched saturated hydrocarbon radicals having from one to six carbon atoms. Representatives of such groups are methyl, ethyl, n-propyl, isopropyl, n-butyl, isobutyl, sec-butyl, t-butyl, the pentyl isoforms, hexal isoforms and the like.

(LOWER ALKYL)THIO

The term "(lower alkyl)thio" refers to a lower alkyl group as defined above, attached to the parent molecular moiety through a sulfur atom. Typical (lower alkyl)thio groups include methylthio, ethylthio, propylthio, iso- propylthio, and the like.

ALKOXY

Alkoxy as represented by —$OR_1$ when $R_1$ is ($C_1$–$C_8$) alkyl refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, n-hexoxy, isohexoxy, n-heptoxy, isoheptoxy, and n-octoxy and the like.

LOWER ALKOXY

The term "lower alkoxy" denotes an alkyl group as defined above, attached to the patent molecular moiety through an oxygen atom. Representatives of such groups include methoxy, ethoxy, butyoxy and the like.

ALKENYL

Alkenyl refers to a radical of an aliphatic unsaturated hydrocarbon having at least one double bond and includes both branched and unbranched forms such as ethenyl, (—CH=$CH_2$), 1-methyl-1-ethenyl, 1-propenyl, (—$CH_2$—CH=$CH_2$), 2-propenyl, 1-butenyl, 2-butenyl, 3-butenyl, 2-methyl-1-butenyl, 1-pentenyl, allyl, 3-pentenyl, 4-pentenyl, 1-methyl-4-pentenyl, 3-methyl-1-pentenyl, 3-methyl-allyl, 1-hexenyl, 2-hexenyl, 3-hexenyl, 4-hexenyl, 1-methyl-4-hexenyl, 3-methyl-1-hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl, or 3-octenyl and the like.

ALKYNYL

Alkynyl refers to a monovalent branched or unbranched hydrocarbon radical containing at least one carbon-carbon triple bond, for example ethynyl, propynyl, and the like.

CYCLOALKYL

The parenthetical term ($C_{n-m}$ cycloalkyl) is inclusive such that a compound of ($C_{3-10}$) would include radicals of a saturated cyclic hydrocarbon of 3 to 10 carbons in their cyclic chain. The term may also include alkylsubstituted cycloalkyl, such as cyclopropyl, 2-methylcyclopropyl, 2,2-dimethylcyclopropyl, 2,3 diethylcyclopropyl, 2-butylcyclopropyl, cyclobutyl, 2-methylcyclobutyl, 3-propylcyclobutyl, cyclopentyl, 2,2-dimethylcyclopentyl, cyclohexyl, cycloheptyl, cyclooctyl and cyclodecyl and the like. Each of these moieties may be substituted as appropriate.

HETEROALKYL

"Heteroalkyl" refers to a alkyls as described above, only where one, two or three non-adjacent carbon atoms are replaced by heteroatoms such as nitrogen, sulfur and oxygen.

ARYL ($C_{6-12}$) aryl, refers to a 6 to 12 carbon atom base structure, one or two fused or nonfused aromatic rings, that may be optionally substituted or substituted with one to 3 hydroxy, $C_1$–$C_3$ alkoxy, $C_1$–$C_3$ alkyl, trifluoromethyl, fluoro, chloro, or bromo groups. Examples of "aryl" are: phenyl, m-methylphenyl, p-trifluoromethylphenyl, α-naphthyl, β-naphthyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)-tolyl, 4-isopropyl-2,6-xylyl, 3-propyl-4-ethylphenyl, (2,3,4-, 2,3,6-, or 2,4,5-) trimethylphenyl, (o-, m-, or p-)fluorophenyl, (o-, m-, or p-trifluoromethyl)phenyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3-fluorophenyl, (3- or 4-)chloro-2-fluorophenyl, (o-, m-, or p-,)trifluorophenyl, (o-, m-, p-)ethoxyphenyl, (4- or 5-)chloro-2-methioxy-phenyl, and 2,4-dichloro(5- or 6-)methylphenyl and the like. Each of these moieties may be substituted as appropriate.

ALKYLARYL

Alkylaryl refers to alkyl chains of one to 8 carbon atoms and isomeric forms thereof which are substituted with aryl groups of 6 to 12 carbon atoms as described above.

HETEROCYCLICS

Examples of heterocyclics include: (2-, 3-, or 4-)pyridyl, imidazolyl, indolyl, $N^{in}$-formyl-indolyi, $N^{in}$-$C_2$–$C_5$alkyl-C (O)-indolyl, [1,2,4]-triazolyl, (2-, 4-, 5-)pyrimidinyl, (2-, 3-)thienyl, piperidinyl, pyrrolyl, pyrrolinyl, pyrrolidinyl, pyrazolyl, pyrazolinyl, pyrazolidinyl, imidazolyl, imidazolinyl, imidazolidinyl, pyrazinyl, piperazinyl, pyridazinyl, oxazolyl, oxazolidinyl, isoxazolyl, isoxazolidinyl, morpholinyl, thiazolyl, thiazolidinyl, isothiazolyl, isothiazolidinyl, quinolinyl, isoquinolinyl, benzimidazolyl, benzothiazolyl, benzoxazolyl, furyl, puryl, phenazyl, carbazolyl, thienyl, and benzothienyl, thienyl, indolyl, iso-quinolyl and the like. Each of these moieties may be substituted as appropriate.

HETEROARYL

Heteroaryl refers to a one or two ring structure, of 5–12 ring atoms, where a minimum of one ring is aromatic, only where one, two or three non-adjacent carbon atoms are replaced by heteroatoms such as nitrogen, sulfur and oxygen. Examples can include pyridine, thiophene, furan, pyrimidine, 2-pyridyl, 3-pyridyl, 4-pyridyl, 2-pyrimidinyl, 4-pyrimidinyl, 5-pyrimidinyl, 3-pyridazinyl, 4-pryidazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl,2-thiazolyl, 4-thiazolyl, 5-thiazolyl, 2-indolyl, 3-indolyl, 3-indazolyl, 2-benzoxazolyl, 2-benzothiazolyl, 2-benzimidazolyl, 2-benzofuranyl, 3-benzofuranyl, 2-furanyl, 3-furanyl, 2-thienyl, 3-thienyl, 2-pyrrolyl, 3-pyrrolyl, 1,2,4-oxadiazol-3-yl, 1,2,4-oxadiazol-5-yl, 1,2, 4-thiadiazol-3-yl, 1,2,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 1-purinyl, 3-isothiazolyl, 4-isothiazolyl and 5-isothiazolyl. Each of these moieties may be substituted as appropriate.

CHIRALITY

It will be apparent to those skilled in the art that compounds of this invention may contain one or more chiral centers and may exist in optically active forms including cis-/trans- and/or R- and S- isomeric forms and mixtures thereof. The scope of this invention includes all of these forms, the enantiomeric or diastereomeric forms of the compounds, including optically active forms, in pure form or as mixtures of enantiomers or diastereomers including cis-/trans-isomeric forms. The therapeutic properties of the compounds may to a greater or lesser degree depend on the stereochemistry of a particular compound. Resolution can be accomplished using resolving agents such as optically active dibenzoyltartaric acid, camphorsulfonic acid, bis-o-toluoyltartaric acid, tartaric acid, and diacetyl tartaric acid.

OPTICAL PURITY is sometimes referred to as "% ee."

Procedures and Compounds of the Invention

The procedures below refer to compounds and formula identified in the CHARTS.

PROCEDURES, REACTIONS AND COMPOUNDS OF CHART G

General Description of the Reactions

All of the variables for the procedures described below are defined above, in the Summary of the Invention and in the Definitions. More preferred substituents are disclosed below.

STEP 1. (Citrazinic acid→1 G)

The starting material, dichloroisonicotinic acid, is a known compound and is readily prepared from commercially available citrazinic acid.

The methods of preparation and range of acceptable conditions are known and contained in the following references: M. E. Baizer, M. Dub, S. Gister, N. G. Steinberg, *J. Am. Pharm. Assoc*, 1956, 45, 478–480; The use of tetraalkylammonium and tertiary amine salts in this type of reaction is described in Chemical Abstracts, CA 97, 216024 and East German patent, DD 154,538 by E. Schroetter, H. Schick, H. Niedrich, P. Oehme, and L. Piesche. See also, W. H. Levelt and J. P. Wibaut, *Rec. Trav. Chem*, 1929, 44,466.

In the preferred method, citrazinic acid is heated with phosphorus oxychloride and a tetraalkylammonium chloride or tertiary amine hydrochloride, most preferably tetramethylammonium chloride, to a temperature between 120° and 140° for about 12 to 24 hours. The mixture is then reacted with water to yield the product, 1CPT.

STEP 2. (1G→2G)

2,6-dichloroisonicotinic acid is dissolved or suspended in an ethereal solvent such as diethyl ether, tetrahydrofuran, or 1,2-dimethoxyethane and reacted with an excess of ethylmagnesium halide or ethyllithium in diethyl ether or tetrahydrofuran solution at a temperature between about −30° and about +10°. The excess ethyl magnesium halide or ethyllithium is decomposed by reaction with a dilute acid such as hydrochloric acid, or by reaction first with an ester such as methyl formate or a ketone such as acetone, followed by reaction with a dilute acid such as hydrochloric acid.

Alternatively, the 2,6-dichloroisonicotinic acid may be converted into the acid chloride by reaction with thionyl chloride, or phosphorus pentachloride, and then converted into the Weinreb amide. See, S. Nahm and S. M. Weinreb, *Tet. Lett*, 1981, 3815–3818. The Weinreb amide is then dissolved in reacted with an ethereal solvent such as diethyl ether, tetrahydrofuran, or 1,2-dimethoxyethane and reacted with an excess of ethylmagnesium halide or ethyllithium in diethyl ether or tetrahydrofuran solution at a temperature between about −30° and about +10°. The product is then isolated after reaction of the intermediate complex with a dilute acid such as hydrochloric acid. Preferred $R_6$ is lower alkyl, including $C_{1-4}$alkyl and ethyl, aryl and substituted aryl, alkylaryl,and substituted alkylaryl, including benzyl and substituted benzyl, $C_{3-10}$ cycloalkyl, heteroaryl, or substituted heteroaryl, preferably $C_{1-4}$ alkyl, ethyl, benzyl.

STEP 3. (2G→3G)

The alkyl ketone, referred to in CHART G p. 1, as 2 G, is reacted with an alcohol or a diol in the presence of trimethylchlorosilane. Alcohols may be diols such as ethylene glycol, 1,3-propanediol, or 2,2-dimethyl-1,3-propanediol, or alcohols such as methanol. The preferred alcohol is ethylene glycol. When ethylene glycol is used the ethylene ketal is produced, other ketals may be produced with other alcohols. A solvent such as methylene chloride may be added. The reaction is run at a temperature between about 0° and about 60°, preferably at about 40°. Preferred $R_6$ is lower alkyl, including $C_{1-4}$alkyl and ethyl, aryl and substituted aryl, alkylaryl,and substituted alkylaryl, including benzyl and substituted benzyl, $C_{3-10}$ cycloalkyl, heteroaryl, or substituted heteroaryl, preferably $C_{1-4}$ alkyl, ethyl, benzyl.

STEP 4. (3 G→4G)

The compound in CHART G p.1 labeled 3 G is reacted with a sodium or potassium alkoxide, either in an excess of the alcohol or a solvent such as tetrahydrofuran or 1,2-dimethoxyethane. The reaction may be run at a temperature between about 20° and 80°. The alkoxide, or the preferred $R_1$ group of CHART G, may be any of the previously defined lower alkyl, cycloalkyl, $C_{3-10}$ cycloalkyl, alkenyl, aryl, and aryalkyl, including benzyl and substituted benzyl, groups. The more preferred $R_1$ groups are methyl and benzyl.

STEP 5a (optional) and STEP 5b. (4G→5G)

STEP 5a. Ortho-directed metallation reactions have been reviewed, see V. Snieckus, Chem. Rev., 1990, Vol. 90, pp. 879–933, incorporated by reference.

The compound in CHART G p.1 labeled 4 G is dissolved in a solvent and reacted with an alkyllithium base or arylllithium base to form the pyridyl anion. The resulting anion is then reacted with an electrophile and the product is isolated after further reaction with a dilute acid. Suitable solvents for the reaction are ethers such as diethyl ether, tetrahydrofuran, or 1,2-dimethoxyethane or hydrocarbons such as toluene, hexane, heptane, cyclohexane, or isooctane, or mixtures of any of these or similar solvents.

The alkyllithium may be methyllithium, n-butyllithium, sec-butyllithium or t-butyllithium. The reaction temperature may be between about −40° and about +50°. The electrophile may be an alkyl halide such as methyl iodide, dimethyl sulfate, chloromethylmethyl ether, benzyl chloromethyl ether, or benzyl bromide; aldehydes or ketones such as formaldehyde, acetone, benzaldehyde or other similar compounds; or amides such as formamides including dimethylformamide, N-formylpiperidine, or N formylmorpholine or N-methylformanilide or similar formamides. The acid used for product isolation may be hydrochloric acid, acetic acid, sulfuric acid, or other moderate to strong acids.

The preferred solvent is heptane, the preferred base is n-butyllithium, and the preferred amide is N-formylpiperidine. The reaction is preferably run between about −5° and about +5°. Purification of the product may be accomplished by crystallization, chromatography, or through the formation of the bisulfite addition compound, which may be decomposed by reaction with either acid or base.

Note that STEP 5a may be omitted, STEP 5b may be used without STEP 5a, to produce 5G.

STEP 5b.

The aldehyde of STEP 5a is reduced to the alcohol with a hydride reducing agent such as sodium borohydride. The reaction may be run using an alcohol such as methanol or 2-propanol as the solvent, or may be run under two-phase conditions with water and an organic phase consisting of heptane, methylene chloride or methyl t-butylether, or mixtures of these and similar solvents. A phase transfer catalyst such as tetrabutylammonium chloride may be added but is not essential.

STEP 5a and STEP 5b. (4 G→5 G)

Preferred $R_2$, shown in CHART G, may be H, or a) any optionally substituted $C_{1-8}$alkyl, alkylaryl, $C_{1-8}$alkyl-aryl, including $C_{1-8}$alkyl-$C_6$aryl, substituted benzyl and unsubstituted benzyl; b) —C(O)—$R_3$, or c) —C($R_7$)$_2$—O—$R_3$ where each $R_7$ is independent of the other; and where $R_3$ and $R_7$ are defined above, in the Summary of Invention. This series of reactions proceeds with CHART G p.2, STEP 6, immediately below, only when $R_2$ is b) —C(O)—$R_3$, or c) —C($R_7$)$_2$—O—$R_3$ where each $R_7$ is independent of the other. When $R_2$ is H or any optionally substituted $C_{1-8}$alkyl, alkylaryl, $C_{1-8}$alkyl-aryl, including $C_{1-8}$alkyl-$C_6$aryl, substituted benzyl and unsubstituted benzyl; then the reactions proceed according to CHART M-G and CHART M-M and may result in the production of mappicine or mappicine analogues.

STEP 6. (5 G→6 G)(CHART G —continued)

The alcohol is reacted with a base, and an alkylating agent in an appropriate solvent to yield the product. Bases may be hydrides such as sodium hydride or potassium hydride, or alkoxide bases such as potassium t-butoxide.

Suitable solvents are ethereal solvents such as tetrahydrofuran or 1,2-dimethoxyethane or alcohols such as t-butanol. The temperature may be between about 15° and about 80°. The preferred base is potassium t-butoxide and the preferred solvents are THF or MTBE at a temperature preferably between about 20° and about 40°.

Alternatively, the reaction may be performed under phase transfer conditions using water and an organic solvent such as methylene chloride, or hydrocarbons such as hexane, heptane, or toluene or similar solvents. The base may be a hydroxide such as sodium or potassium hydroxide, or sodium or potassium carbonate. A phase transfer catalyst such as tetrabutylammonium chloride may be added and the preferred temperature range is between about 10° and about 30°.

ALTERNATIVE STEPS

There are 2 different Step 7 reactions, series 7GG and 7GA; 3 different Step 8 reactions, series 8GG, 8GA, 8GB; 3 different Step 9 reactions, series 9GG, 9GA, 9GB and 2 different step 10 reactions, series 10GG and 10GA followed by a Step 10 resolution procedure. See Chart G, p. 2, 3, 4.

STEP 7 GG and STEP 10 GA. (6 G→7 GG) and (9 GA→10 G).

Carbonylation reactions of aryl halides catalyzed by palladium-zero are well known, see, J. K. Stille and P. K. Wong, *J. Org. Chem.*, 1975, 40, 532–534, but aryl chlorides generally have low reactivity in these reactions. In contrast to simple aryl chlorides, 2-chloropyridines are known to undergo facile insertion reactions with palladium-zero. Various coupling reactions of 2-chloropyridines catalyzed by palladium-zero are known but carbonylation reactions of 2-chloropyridines catalyzed by palladium-zero have not been reported in the literature.

Compounds represented by 6G are reacted with carbon monoxide and an alcohol in the presence of a soluble palladium II salt (such as palladium acetate), a phosphine ligand (such as 1,3-bisdiphenylphosphinopropane), and a base such as sodium or potassium acetate, sodium or potassium carbonate, triethylamine, or tri n-butylamine in a polar aprotic solvent such as dimethyl formamide or acetonitrile.

The preferred $R_3$ group, shown in CHART G p.2 & 3, may be any of the previously defined, H, lower alkyl, cycloalkyl, alkenyl, aryl, and aryalkyl, including benzyl and substituted benzyl, groups. The more preferred $R_3$ groups are methyl and benzyl.

The preferred $R_4$ group of the alcohol, shown in CHART G p.2 & 3, may be any of the previously defined, H, lower alkyl, cycloalkyl, alkenyl, aryl, and aryalkyl, including benzyl and substituted benzyl, groups. The more preferred $R_4$ group is n-propyl. The temperature range is between about 50° to and about 100°.

The preferred $R_7$ group is independently H, lower alkyl, aryl, alkylaryl, substituted aryl, substituted alkylaryl, or two $R_7$ groups may be combined to form cyclopentane or cyclohexane or substituted derivatives thereof.

Some references describing the insertion reactions mentioned in STEP 7, above, are: a) K. Isobe and S. Kawaguchi, Heterocycles, 1981, 16, 1603–1612; b) N. Sato, A. Hayakawa, and R Takeuchi, *J. Het. Chem.* 1990, 503–506; c) M. Ishikura, M. Kamada, and M. Terashima, *Synthesis*, 1984, 936–938; and d) K. Isobe, K. Nanjo, Y. Nakamura, and S. Kawaguchi, *Bul. Chem. Soc. Japan*, 1986, 59, 2141–2149.

STEP 7 GA and STEP 8 GG. (6 G→7 GA) also for (7 GG→8 GG)

The ketal is hydrolyzed by reaction with water in the presence of a strong acid such as trifluoroacetic acid. The trifluoroacetic acid concentration may be between about 50% and 90% and the reaction temperature between about 15° and about 30°. Alternatively, the ketal may be removed by an exchange reaction with a ketone such as acetone or 2-butanone catalyzed by a strong acid such as p-toluenesulfonic acid or an acidic ion exchange resin such as amberlyst A-15 resin. The preferred temperature for the exchange reaction is about the reflux temperature of the ketone.

STEP 8GA. (7GA→8GA)

Compound 8GA is dissolved in a solvent and reacted with a vinyllithium or a vinylmagnesium halide. Suitable solvents are ethers such as diethyl ether, tetrahydrofuran, 1,2-dimethoxyethane, or MTBE, either alone or as mixtures, or as mixtures with hydrocarbons such as toluene, heptane, or cyclohexane. The reaction temperature may be between about −78° and about 25°. The product is isolated after further reaction with a dilute acid such as hydrochloric, sulfuric, or acetic acids. The preferred reagent is vinylmagnesium bromide in tetrahydrofuran as the solvent at a temperature of about −40° to about 25° followed by quenching with hydrochloric acid. Preferred $R_5$ is independently, H, lower alkyl, aryl, substituted aryl, or two $R_5$ groups may be combined to form cyclopentane or cyclohexane, or substituted derivatives thereof.

STEP 8GB and STEP 9GG. (7 GA→8 GB and 8 GG→9 GG)

The Wittig reaction is performed by reaction the ketone with an ylide solution prepared from a methyl triph-enylphosphonium salt, preferably the bromide and a strong base, such as n-butyllithium, potassium t-butoxide, or potassium bis trimethylsilylamide, in a solvent such as diethyl ether, tetrahydrofuran, 1,2-dimethoxyethane, or DMF. The preferred base is potassium bis trimethylsilylamide and the preferred solvent is DMF. The reaction temperature is between about −5° and about 25°. Reaction time is between about 5 min and about 2 hours.

STEP 9GA. (8GA→9GA)

9GA is dissolved in a solvent and reacted with ozone to produce an intermediate. Depending on the solvent composition, this intermediate may be an ozonide or a mixture of hydroperoxides. The intermediate is reacted with a suitable reducing agent to produce the product, either directly or stepwise through the intermediacy of an aldehyde. The temperature for the reaction may be between about −78° and about 25°. Suitable solvents for the reaction are chlorinated hydrocarbons such as methylene chloride, chloroform, carbon tetrachloride, 1,2-dichloroethane, or other multiply chlorinated ethane or ethylene derivatives, either alone, as mixture, or as mixtures with alcohols such as methanol. The preferred solvent is a mixture of methylene chloride and methanol at a temperature from about −78° to about −40° for the initial reaction with ozone, and a temperature of about 0° to 25° for the reduction of the intermediate. The preferred reducing agent is sodium borohydride.

STEP 9GB and STEP 10GG. (8 GB→9 GA and 9 GG→10 GG).

The alkene is converted into the diol by osmylation under standard conditions, see, V. VanRheenen, R. C. Kelley, and D. Y. Cha, Tet. Lett., 1976, 1973, with catalytic osmium tetroxide and a stoichiometric cooxidant such as trimethylamine N-oxide or N-methylmorpholine-N-oxide in either aqueous THF or, preferably, t-butanol as the solvent. The reaction temperature may be between about 15° and about 50°, preferably about 40°, for about 12–48 hours.

An alternative to the racemic osmylation is the use of an asymmetric osmylation, as described by Sharpless, for the conversion of 9CPT directly into 10G (R) or (S). Specific references for the Sharpless asymmetric osmylation are: G. A. Crispino, A. Makita, Z.-M. Wang, K. B. Sharpless, Tet. Lett., 1994, 543–546. G. A. Crispino, K.-S. Jeong, H. C. Kolb, Z.-M. Wang, D. Xu, K. B. Sharpless, J. Org. Chem., 1993, 3785–3786 and the many references cited in this paper. K. B. Sharpless, W. K. Amberg, U.S. Pat. No. 5,227,543. K. B. Sharpless, M. Beller, B. Blackburn, Y. Kawanami, H.-L. Kwong, Y. Ogino, T. Shibata, T. Ukita, L. Wang, PCT WO 92/20677. J. Hartung, K. B. Sharpless, PCT WO 93/07142.

STEP 10. Resolution (10 G→10 G (R or S)).

The racemic diol like 10 G may be treated with an acetylating reagent like vinyl acetate, isopropenyl acetate, acetic anhydride or ethyl acetate in an organic solvent in the presence of a lipase. Possible solvents include ether, or hexane and the lipase may be a *cepaica* like *Pseudomonas cepaica*. Using this process one can obtain a single acetate isomer and a single diol isomer. The reaction is usually conducted between 25° to 45° C. at a substrate concentration of 15–40 mg/mL. The products of the reaction can be separated by crystallization using common organic solvents or by conventional silica gel chromatography. The optical purity (% ee) of each enantiomer can be determined by NMR with chiral shift reagents or by chiral HPLC analysis.

STEPS 11–14.

The following reactions may be run with the single enantiomer, or racemic mixtures or other ratios of enantiomeric mixtures. The product of the reactions will depend on the starting materials. CHART G p. 4 & 5 and the steps below refer to a single enantiomer for convenience and by way of example. The single enantiomer is usually referred to by a capitol letter "R" or "S." One example is "10 G (R)." The racemic mixture is usually referred to by a number followed by the capitol letter "G." One example is "10G." See CHART G. The reactions of this invention are, of course, not limited to what is shown in the Charts, for example, CHART G does not show the reaction STEPS 11 through 13 for the racemic mixtures but it is implied in the CHART and described herein. Similarly the "R" series is not as completely shown as the "S" series. The CHARTS are descriptive aids only and do not represent the complete invention.

STEP 11. (10G→11G)

The diol may be oxidized to the hydroxy aldehyde using oxidation under Swern type conditions such as DMSO, oxalyl chloride and triethylamine in an aprotic solvent such as methylene chloride at a temperature ranging from about −78° to about 25°. Alternatively, the oxidation can be done with sodium hypochlorite solution catalyzed by TEMPO or a substituted TEMPO such as 4-acetoxy-TEMPO in a two phase system consisting of water and an aprotic solvent such as methylene chloride. The reaction temperature is preferably between about −5° and about +25° and the reaction time is between about 30 min and about 2 hours.

Swern type conditions are described in A. J. Mancuso and D. Swern Synthesis, 1981, 165–185. A two phase system consisting of water and an aprotic solvent is described in P. L. Anelli, C. Biffi, F. Montanari, and S. Quici, J. Org. Chem, 1987, 52, 2559–2562. Incorporated by reference.

STEP 12. (11G→12G)

Several variations have been used to convert the hydroxyaldehyde, 11G into 12G. In the first procedure, the hydroxy aldehyde, 11G is oxidized to the hydroxy acid, 12GA-1, with sodium chlorite. The hydroxyacid then can be converted into 12G by reaction with trimethylsilyl iodide in one pot. The advantage of this procedure is the one step conversion of 11G into 12G. Refer to CHART G p. 5, STEP 12, Pathway A, Part 2, path a. The disadvantage of this one step conversion is the relatively low yield and variable reaction times.

A higher yielding procedure removes the benzyl group first, either by hydrogenation or reaction with boron tribromide, and then the methoxy group by reaction with trimethylsilyl iodide. Refer to CHART G p. 5, STEP 12, Pathway A, Part 2, path b-1 and b-2. Obviously, the order of deprotection steps could be reversed.

A second method for the conversion of 11G into 12G changes the order of the oxidation and deprotection steps. Refer to CHART G p. 5, STEP 12, Pathway B. The benzyl group is removed by hydrogenation to yield the lactol. The lactol is then oxidized with sodium hypochlorite catalyzed by TEMPO. Cleavage of the methoxy group is done as before with trimethylsilyl iodide. Refer to CHART G p. 5, STEP 12, Pathway B, Parts 1, 2, and 3. The advantage of this sequence is the avoidance of the sodium chlorite oxidation and the hazards associated with it.

Pathways A and B are described in more detail below, Pathway B is preferred. See CHART G p. 4 & 5.

STEP 12. Pathway A. (11G→12G Pathway A)

Pathway A has two parts, part 1 and part 2. Part 2 follows part 1. Part 2 of Pathway A also has 2 paths, path a and path b. Path a of Pathway A, part 2, has only one step. Path b of Pathway A part 2 has two steps. See CHART G, p. 4, note that only one stereoisomer is shown, the other stereoisomers and racemic mixtures are suggested.

Part 1.

Oxidation to form the hydroxy acid is done preferably with sodium chlorite using conditions described in the literature. See, B. S. Bal, W. E. Childers, H. W. Pinnick, Tetrahedron, 1981, 2091–2096. Other additives, such as hydrogen peroxide or sulfamic acid, have also been used to prevent the formation of chlorine dioxide. This produces 12 GA-1.

Part 2.

Path a.

One step removal of the benzyl and methyl groups is done with trimethylsilyl iodide, either preformed or generated in situ from trimethylsilyl chloride and sodium iodide in methylene chloride or acetonitrile. See, T. Morita, Y. Okamoto, H. Sakurai, J. C. S. Chem. Comm, 1978, 874–875, and M. E. Jung and M. A. Lyster, J. Am. Chem. Soc., 1977, 99, 968. Pyridine may be added but is not required. The reaction temperature is between about 15° and 50° for between 12 and 48 hours. This produces 12G.

Path b.

Part 1 of Path b-1.

The two step removal of the benzyl and methyl groups can be done in two ways. The benzyl group is removed by hydrogenation over a catalyst, preferably a palladium catalyst supported on carbon or other porous substrate, or palladium black. The solvent is preferably an alcohol, most preferably methanol. The reaction is done at about 15° to about 40° under an atmosphere of hydrogen at a pressure of about 1 atmosphere to about 4 atmospheres for about 2-four hours.

Alternatively, the benzyl group may be removed by reaction with boron tribromide in a solvent such as methylene chloride at about −5° to about 20° for about 30 minutes to about 2 hours. Produces 12 GA-2, alternately labeled 12 GB-2.

Part 2 of Path b-2.

Cleavage of the methoxy group to yield 12G may be accomplished with trimethylsilyl iodide, as described above. (This step is the same as the third step of Pathway B, below.)

STEP 12. Pathway B. (11G→12G, Pathway B)

Pathway B has 3 steps.

Part 1.

The benzyl, or other appropriate group, is removed by hydrogenation over a catalyst, preferably a palladium catalyst supported on carbon or other porous substrate, or palladium black. The solvent is preferably an alcohol, most preferably methanol. The reaction is done at about 15° to about 40° under an atmosphere of hydrogen at a pressure of about 1 atmosphere to about 4 atmospheres for about 12 to about 96 hours. This produces 12 GB-1.

Part 2.

The lactol is then oxidized under the same conditions for the formation of the hydroxy aldehyde:using either oxidation under Swern conditions such as DMSO, oxalyl chloride and triethylamine in an aprotic solvent such as methylene chloride at a temperature ranging from −78° to about 25°. Alternatively, the oxidation is done with sodium hypochlorite solution catalyzed by TEMPO or a substituted TEMPO such as 4-acetoxy-TEMPO in a two phase system consisting of water and an aprotic solvent such as methylene chloride. The reaction temperature is between about −5° and about +25° and the reaction time is between about 30 minutes and 2 hours. This produces 12 GB-2 alternately labeled 12 GB-1.

Part 3.

Removal of the methyl group is done with trimethylsilyl iodide, either preformed or generated in situ from trimethylsilyl chloride and sodium iodide, in methylene chloride or acetonitrile. The conditions are described above. This produces 12 G.

STEP 13. (12G→13G)

12G is reacted with an acrylate ester, such as methyl, ethyl, or t-butyl acrylate in the presence as a base such as potassium hydride, sodium hydride, potassium t-butoxide, sodium carbonate, potassium carbonate, cesium carbonate, or tertiary amines such as diisopropylethyl amine in a polar aprotic solvent such as dimethyl sulfoxide, DMF, or acetonitrile at a temperature between about 20° and 100°. See CHART G, p. 5. The preferred conditions are reaction with t-butyl acrylate and cesium carbonate in DMSO at about 50° The product may be isolated as the toluene solvate. This gives the ketoester, compounds 13G.

STEP 14. (13G→14G)

The ketoester, which may exist primarily or exclusively in the enol form, is converted into 14G by reaction with a strong acid such as trifluoroacetic acid at a temperature of about 80° to about 110° for about 10 minutes to about 6 hours. A solvent such as toluene may be added. The preferred conditions are a mixture of toluene and trifluoroacetic acid at 100–110° for 1–4 hours.

All references cited in the description of the Charts are incorporated by reference. Using the procedures described above and substituting appropriate starting materials anyone reasonably skilled in the art should be able to make the compounds and reactions of this invention. One embodiment of this invention is described by the reactions, procedures and structures of CHART CPT-11. This embodiment only illustrates and should not limit the invention in any manner.

PROCEDURES, REACTIONS AND COMPOUNDS OF CHART CPT-11 STEP 1.
(citrazinic acid→1CPT)

Citrazinic acid (152.0 g, 0.98 mole) and tetramethylammonium chloride (107.71 g, 1.02 mole) were suspended in phosphorus oxychloride (450 g, 273 mL, 2.9 mole) and heated in a 130° C. bath. The solids dissolved with a slight exotherm when the internal temperature reached about 75° C., yielding a clear brown solution. The reaction was heated at 130° C. for 18 hours, then heated to 145° C. for 2 hours. The mixture was cooled to room temperature, poured onto 2 kg of ice, and stirred for 2 hours. The solids were dissolved in 1.5L of ethyl acetate. The organic solution was dried over sodium sulfate, filtered, and evaporated to yield 146.9 g (78%) of a light brown solid.

mp 195–197° C. (dec). (lit.[1] mp. 205–207° C.). $^1$H NMR (300.13 MHz, DMSO-$d_6$) δ 7.80 (s, 2H). $^{13}$C NMR (75.47 MHz, DMSO-$d_6$) δ 122.87, 144.60, 150.13, 163.66. Nominal mass spectrum calculated m/z 192, found m/z 192.

References.
1. M. E. Baizer, M. Dub, S. Gister, N. G. Steinberg, J. Am. Pharm. Assoc, 1956, 45, 478–480.
2. The use of tetraalkylammonium salts in this type of reaction is described in DDR patent 154538.

STEP 2. (1CPT→2CPT)

1CPT (6.6 g, 0.034 mole) was mixed with 82 mL of THF and the mixture cooled to −40° C. Ethylmagnesium chloride (52 mL, 104 mmole, 2M in THF) was added over the course of about 15 min, keeping the internal reaction temperature at less than −30° C. The cooling bath was removed, and the resulting dark brown mixture was allowed to warm to 0° C. and stirred at 0° C. for one hour. The reaction mixture was recooled to −25° C. and methyl formate (3.2 mL, 52 mmole) was added. After 15 min at −25° C., 20 mL of 6M hydrochloric acid was added and the mixture was allowed to warm to room temperature. The phases were separated and the lower aqueous phase was extracted 3×10 mL with THF. The combined THF phases were washed 2× with a mixture of 15 mL 1N NaOH and 15 mL sat NaCl, and then once with 15 mL of sat NaCl solution. The organic phase was dried over sodium sulfate and then concentrated to an oil. Toluene (50 mL) was added and the mixture was concentrated to an oil, and the process repeated to yield 6.01 g (84%) of brown oil which crystallized under vacuum.

mp 60–63° C. $^1$H NMR (300.13 MHz, CDCl$_3$) δ 1.17 (t, J=7.1 Hz, 3H), 2.88 (q, J=6.6 Hz, 2H), 7.61 (s, 2H). $^{13}$C NMR (75.47 MHz, CDCl$_3$) δ 7.50, 32.61, 120.88, 147.66, 151.83, 197.15. Nominal mass spectrum calculated m/z 204, found m/z 204.

STEP 3. (2CPT→3CPT)

2CPT (90.2 g, 0.44 mole), ethylene glycol (650 mL), and trimethylsilyl chloride (140 mL, 1.1 mole) were mixed and stirred at room temperature. White crystals gradually formed in the mixture. After about 12 hours the reaction was complete. The reaction was neutralized by the addition of 1L of 1N NaOH solution and extracted 3×250 mL with 1:1 ethyl acetate/heptane. The organic extracts were combined, dried over sodium sulfate and evaporated. The crystalline residue was dried under high vacuum to yield 109.71 g (100%) of the product.

mp 91° C. $^1$H NMR (300.13 MHz, CDCl$_3$) δ 0.80 (t, J=7.4 Hz, 3H), 1.78 (q, J=7.4 Hz, 2H), 3.72 (t, J=7.0 Hz, 2H), 3.99 (t, J=7.0 Hz, 2H), 7.27 (s, 2H). $^{13}$C NMR (75.47 MHz, CDCl$_3$) δ 7.45, 32.77, 65.10, 108.94, 120.30, 150.57, 158.06. Nominal mass spectrum calculated m/z 248, found m/z 248.

STEP 4. (3CPT→4CPT)

3CPT (57.5 g, 0.23 mole) was dissolved in methanol (170 mL). Sodium methoxide (80 mL, 0.35 mole, 25% wt soln. in methanol) was added and the reaction brought to reflux in an 85° C. oil bath. After 20 hours the reaction mixture was allowed to cool to room temperature and then quenched with 250 mL of water. The two-phase mixture was diluted with 200 mL of methylene chloride and partitioned. The aqueous phase was extracted with two more 100 mL portions of methylene chloride. The organic extracts were combined, dried over MgSO4, filtered, and concentrated to an amber oil which crystallizes upon seeding to yield 50.43 g (89%) as a light yellow solid.

mp 47° C. $^1$H NMR (300.13 MHz, CDCl$_3$) δ 0.88 (t, J=7.4 Hz, 3H), 1.85 (q, J=7.5 Hz, 2H), 3.78 (t, J=6.9 Hz, 2H), 3.93 (s, 3H), 4.02 (t, J=7.1 Hz, 2H), 6.73 (s, 1H), 6.98 (s, 1H). $^{13}$C NMR (75.47 MHz, CDCl$_3$) δ 7.62, 32.53, 54.04, 64.79, 106.25, 109.23, 113.83, 148.33, 157.27, 163.94. Nominal mass spectrum calculated m/z 243, found m/z 244 (m+1).

STEP 5. (4CPT→5CPT)

4CPT (73.05 g, 0.299 mole) was dissolved in 1400 mL of heptane and cooled to −10° C. n-Butyllithium (294 mL, 0.588 mole, 2.5M in hexane) was added over 10 min keeping the internal temperature <5° C. The orange mixture is stirred at 0° C. for 30 min after completion of the butyllithium addition. The mixture was then cooled to −30° C. and N-formylpiperidine (66.0 mL, 0.588 mole) was added. The mixture was allowed to warm to 0° C. and stirred at 0° C. for 1 hr. The deep red mixture was quenched by the addition of 600 mL of 1N HCl. The phases were separated and the aqueous phase extracted with 2×250 mL of MTBE. The organic phases were combined to yield a solution of 5aCPT. A portion of this solution was chromatographed on silica using 4:1 hexane/ethyl acetate to yield a purified sample of 5aCPT for characterization.

Water (250 mL), tetrabutylammonium chloride (8.3 g, 0.029 mole), and sodium borohydride (11.3 g, 0.29 mole) were added to the solution of 5aCPT and the mixture was vigorously stirred at room temperature. After about 18 hours the reduction was complete. 20 mL of acetone were added and the mixture was stirred at room temperature for 30 min. The aqueous phase was removed and the organic phase was washed once with 500 mL of water. The organic phase was evaporated to an oil. The oil was chromatographed on 800 g of silica using 4:1 hexane/ethyl acetate. Yield of product was 57.30 g, 71% chemical. 15.0 g (20%) of essentially pure 4CPT was also recovered.

5aCPT $^1$H NMR (300.13 MHz, $CDC_{l3}$) δ 0.96 (t, J=9.0 Hz, 3H), 2.03 (q, J=9.0 Hz, 2H), 3.75 (m, 2H), 4.00 (m, 2H), 4.00 (s, 3H), 7.13 (s, 1H), 10.44 (s, 1H). $^{13}$C NMR (75.47 MHz, $CDCl_3$) δ 7.32, 33.28, 54.81, 64.78, 109.66, 114.67, 117.20, 150.83, 157.52, 161.75, 190.80. Nominal mass spectrum calculated m/z 271, found m/z 271.

5CPT mp 49–56° C. $^1$H NMR (300.13 MHz, $CDCl_3$) δ 0.84 (t, J=7.5 Hz, 3H), 1.87 (q, J=7.0 Hz, 2H), 3.74 (m, 2H), 3.92 (s, 3H), 3.97 (m, 2H), 4.72 (s, 1H), 7.05 (s, 1H). $^{13}$C NMR (75.47 MHz, $CDCl_3$) δ 7.46, 33.01, 54.50, 56.16, 64.98, 110.25, 114.53, 119.15, 147.39, 154.50, 163.00. Nominal mass spectrum calculated m/z 273, found m/z 273.

STEP 6. (5CPT→6CPT, CHART CPT p.2)

5CPT (503.98 g, 1.841 mole) was dissolved in 1330 mL of THF in a 12L flask equipped with a mechanical stirrer, an addition funnel, and a thermocouple with adaptor. 1188 mL of 20% solution of potassium t-butoxide solution in THF to the flask, keeping the internal temperature less than 300. The mixture was stirred for 30 min, then benzyl bromide (230.0 mL, 2.117 mole) was added through the addition funnel, keeping the internal temperature less than 30°. After completion of the benzyl bromide addition, the mixture was stirred at 20–30° for 1 hour. After one hour, 38 mL of 40% aqueous dimethylamine solution was added and the mixture was stirred at 20–30° for 30 min. 276 mL of 1N HCl and 2L of ethyl acetate were added and the phases were separated. The organic phase was washed 3×1L with water and then evaporated to an oil. Yield of product: 663.5 g, 99.3% chemical yield.

$^1$H NMR (300.13 MHz, $CDCl_3$) δ 0.75 (t, J=7.4 Hz, 3H), 1.82 (q, J=7.4 Hz, 2H), 3.61 (m, 2H), 3.82 (s, 3H), 3.85 (m, 2H), 4.48 (s, 2H), 4.57 (s, 2H), 6.97 (s, 1H), 7.23 (m, 5H). $^{13}$C NMR (75.47 MHz, $CDCl_3$) δ 7.50, 32.96, 54.47, 62.83, 64.73, 73.20, 110.12, 114.8, 116.42, 127.54, 127.76, 128.24, 138.43, 147.91, 155.62, 163.74. Nominal mass spectrum calculated m/z 363, found m/z 364 (m+1).

There are two different possible STEP 7 reactions, series G and A, and three different possible STEP 8 reactions. See, Chart CPT p.2

STEP 7G. (6CPT→7CPTG)

6CPT (66.45 g, 183 mmole), palladium acetate (2.05 g, 9.13 mmole), DPPP (4.14 g, 10.0 mmole), potassium carbonate (37.86 g, 274 mmole), n-propanol (665 mL) and DMF (332 mL) were charge to a flask. The flask was purged with nitrogen and then with carbon monoxide. The mixture was heated to 90° under an atmosphere of carbon monoxide for about 16 hours. The reaction was cooled and vented. The solids were removed by filtration through celite and the celite was washed with 350 mL of THF. The combined filtrates and washing were concentrated to a volume of about 400 mL. Water (700 mL) and MTBE (700 mL) were added. The aqueous phase was separated and extracted with 350 mL of MTBE. The combined MTBE solutions were extracted 4×350 mL with water, dried over sodium sulfate, and evaporated to yield 68.03 g (89% chem) of a light orange oil after column chromatography (silica gel: 230–400 mesh, eluent: 80:20 heptane/ethyl acetate.

$^1$H NMR (300.13 MHz, $CDCl_3$) δ 0.87 (t, J=7.4 Hz, 3H), 0.98 (t, J=7.4 Hz, 3H), 1.77 (m, 2H), 1.93 (q, J=7.4 Hz, 2H), 3.71 (m, 2H), 3.94 (m, 2H), 3.99 (s, 3H), 4.26 (t, J=6.7 Hz, 2H), 4.59 (s, 2H), 4.74 (s, 2H), 7.29 (m, 5H), 7.82 (s, 1H). $^{13}$C NMR (75.47 MHz, $CDCl_3$) δ 7.5, 10.42, 22.02, 33.08, 54.07, 63.08, 64.72, 66.98, 73.29, 110.26, 117.05, 122.14, 127.51, 127.99, 128.22, 138.45, 144.70, 153.62, 163.88, 165.29. Nominal mass spectrum calculated m/z 415, found m/z 416 (m+1).

Step 7A. (6CPT→7CPTA)

6CPT (50.0 g, 0.137 mole) was dissolved in 50% aqueous trifluoroacetic acid (250 mL) and stirred at room temperature for 48 hrs. Water (200 mL) and ethyl acetate (200 mL) were added. The phases were separated and the aqueous phase was extracted with ethyl acetate (3×200 mL). The combined organics were washed with saturated sodium bicarbonate solution (500 mL) until residual TFA is removed and then washed with water (200 mL). The organic layer was dried over anhydrous magnesium sulfate, filtered, and concentrated to give 42.6 g (97%) of product.

$^1$H NMR (300.13 MHz, $CDCl_3$) δ 1.04 (t, 7.2 Hz, 3H), 2.71 (q, 7.2 Hz, 2H), 3.95 (s, 3H), 4.47 (s, 2H), 4.56 (s, 2H), 6.77 (s, 1H), 7.29 (m, 5H). $^{13}$C NMR (75.47 MHz, $CDCl_3$) δ 7.39, 36.15, 54.56, 63.16, 73.43, 113.35, 115.73, 127.86, 127.97, 128.51, 137.50, 147.81, 153.07, 161.38, 204.47. Nominal mass spectrum calculated m/z 319, found m/z 320 (m+1).

There are 3 possible different STEP 8 reactions, series G, A and B, see Chart CPT p.2 & 3

STEP 8G. (7CPTG→8CPTG)

7CPTG (68.02 g, 163.7 mmole) was dissolved at room temperature in 384 mL of 50% aqueous TFA. The mixture was stirred at room temperature for 21 hours. 880 mL of water was added and the mixture was extracted 2×500 mL with ethyl acetate. The organic phases were combined and washed 2×500 ml with water and then neutralized with sat. sodium bicarbonate solution. The organic phase was then dried over sodium sulfate and evaporated to yield 59.86 g (98.4%) of the product as a light yellow oil.

$^1$H NMR (300.13 MHz, $CDCl_3$) δ 0.96 (m, 6H), 1.72 (m, 2H), 2.68 (q, J=7.2 Hz, 2H), 3.96 (s, 3H), 4.23 (t, J=6.7 Hz, 2H), 4.42 (s, 2H), 4.58 (s, 2H), 7.24 (m, 5H), 7.48 (s, 1H). $^{13}$C NMR (75.47 MHz, $CDCl_3$) δ 7.55, 10.41, 21.99, 36.21, 54.13, 63.83, 67.22, 73.56, 115.50, 121.49, 127.86, 127.97, 128.19, 128.37, 137.32, 144.87, 150.96, 161.31, 164.54. Nominal mass spectrum calculated m/z 371, found m/z 372 (m+1).

STEP 8A. (7CPTA→8CPTA)

7CPTA (1.00 g, 3.13 mmole) was dissolved in 5 mL THF and cooled to −40° C. under nitrogen. Vinylmagnesium bromide (2.9 mL, 4.4 mmole, 1.5M in THF) was added. The reaction was maintained at −40° C. for one hour, and then allowed to warm to room temperature. After 1 hour at room temperature, the reaction mixture was quenched with saturated aqueous ammonium chloride solution (10 mL) and diluted with ethyl acetate (10 mL). The aqueous layer was extracted with 10 mL of ethyl acetate which was combined with the previous organic layer and dried over sodium sulfate. Filtration and concentration yielded 1.098 g (100% yield) of light amber oil.

$^1$H NMR (300.133 MHz, $CDCl_3$): δ 0.87 (t, J=7.32 Hz, 3H), 1.79–2.00 (m, 2H), 3.93 (s, 3H), 4.54 (s, 2H), 4.83 (s,

2H), 5.16 (dd, J=0.99 Hz, 10.59 Hz, 1H), 5.25 (dd, J=0.99, 17.23 Hz, 1H), 6.01 (dd, J=10.59, 17.23 Hz, 1H), 6.94 (s, 1H), 7.30–7.37 (m, 5H). $^{13}$C NMR (75.468 MHz, CDCl$_3$): δ 7.7, 34.2, 54.5, 62.6, 72.4, 78.0, 114.0, 115.6, 115.9, 127.9, 128.0, 137.2, 143.0, 148.2, 159.2, 163.1. Nominal mass spectrum: calculated m/z 347, found 348 (M+1).

There are three different possible STEP 9 reactions, series G, A and B, see CHART CPT p.3.

STEP 9G. (8CPTG→9CPTG)

Methyltriphenylphosphonium bromide (2.14 g, 6.0 mmole) was dissolved in 15 mL of DMF and stirred at room temperature. Potassium bis-trimethylsilylamide solution (10 mL, 5.0 mmole, 0.5M in toluene) was added and the yellow solution with suspended white solids was stirred at room temperature for 10 min. A solution of 8CPTG (1.48 g, 4.0 mmole) in 5 mL of THF was added all at once, giving a deep red color that rapidly faded to brown. The mixture was stirred for 10 min. Additional ylide solution was added until all of the 8CPTG was consumed. The reaction was quenched by the addition of 10 mL of 1N HCl. 20 mL of MTBE were added and the phases were separated. The aqueous phase was extracted 2×20 mL with MTBE. The combined organic phases were washed 3×20 mL with water, dried over sodium sulfate, and evaporated to a volume of about 15 mL (slight triphenylphosphine oxide crystallization). The solution was chromatographed on silica (about 20 g) with 4:1 hexane/ethyl acetate to yield 1.39 g of product (92% chemical).

$^1$H NMR (300.13 MHz, CDCl$_3$) δ 0.85 (m, 6H), 1.59 (m, 2H), 2.20 (q, J=7.4 Hz, 2H), 3.89 (s, 3H), 4.12 (t, J=6.7 Hz, 2H), 4.33 (s, 2H), 4.42 (s, 2H), 4.89 (s, 1H), 5.06 (s, 1H), 7.17 (m, 5H), 7.35 (s, 1H). $^{13}$C NMR (75.47 MHz, CDCl$_3$) δ 10.43, 12.07, 22.02, 30.23, 53.95, 63.79, 67.00, 73.03, 114.66, 118.67, 121.40, 127.60, 127.90, 128.26, 138.21, 144.49, 147.58, 155.33, 163.11, 165.25. Nominal mass spectrum calculated m/z 369, found m/z 369.

STEP 9A. (8CPTA→9CPTA)

8CPTA (0.500 g, 1.43 mmole) was dissolved in 40 mL of 1:1 methanol:methylene chloride and cooled to −70° C. and then purged with oxygen for 15 minutes. A stream of ozone from a Welsbach ozone generator was passed through the solution until the solution turned blue. The solution was then purged with oxygen for five minutes to remove excess ozone, and then purged for ten minutes with nitrogen. The −78° C. solution was then treated with sodium borohydride (0.250 g, 6.61 mmole) as a solution in 5 mL 50% aqueous methanol. After fifteen minutes, the reaction was allowed to warm to room temperature over the course of an hour. After one hour at room temperature, the reaction was quenched with of 1M HCl solution (10 mL) and partitioned. The aqueous phase was extracted with 20 mL and 10 mL portions of methylene chloride, which were combined with the initial organic layer and dried over sodium sulfate. Filtration and concentration yielded 0.491 g (99% chemical yield) of 9CPTA.

$^1$H NMR (300.133 MHz, CDCl$_3$): δ 0.82 (t, J=7.20 Hz, 3H), 1.86 (dd, J=7.20 Hz, 14.71 Hz, 2H), 3.69 (s, 2H), 3.96 (s, 3H), 4.19–4.31 (m, 2H), 4.28 (s, 2H), 4.59 (s, 2H), 7.20 (s, 1H), 7.40–7.29 (m, 5H). $^{13}$C NMR (75.468 MHz, CDCl$_3$): δ 7.61, 35.44, 54.50, 62.97, 73.40, 75.26, 84.72, 113.71, 114.43, 127.91, 128.18, 128.35, 137.48, 148.56, 158.01, 163.46. Nominal mass spectrum calculated m/z, 351, found m/z.

STEP 9B. (8CPTB→9CPTA) Use similar reagents and conditions described in STEP 9CPTG.

STEP 10G. (9CPTG→10CPTG)

9CPTG (100.0 g, 0.271 mole), trimethylamine N-oxide dihydrate (90.24 g, 0.81 mole) and osmium tetroxide (0.68 g, 2.7 mmole), and 300 mL of t-butanol were charged to a flask. The mixture was heated to 40°. After 24 hours, the mixture was cooled to 20–25°. 300 mL of water and 110 g of sodium metabisulfite were added and the mixture was stirred for 30 min at room temperature. The mixture was extracted 4×200 mL with ethyl acetate. The organic phases were combined and stirred with 50 g of 70–230 mesh silica for 1 hour. The silica was filtered and washed with 100 mL of ethyl acetate. The filtrate was stirred with 100 g of magnesol for 30 min and then the slurry was filtered over 50 g magnesol. The filtrates were combined and concentrated to an oil. 200 mL of toluene and 800 mL of heptane were added and the mixture was allowed to crystallize at −20° for 18 hours. The solids were filtered and washed with 200 mL of heptane. The yield of 10CPT was 83.5 g. Additional 10CPT could be recovered from the filtrates and washings by chromatography.

$^1$H NMR (300.13 MHz, CDCl$_3$) δ 0.74 (t, J=7.4 Hz, 31H), 1.03 (t, J=7.4 Hz, 3H), 1.80 (m, 4H), 3.69 (d, J=11.2 Hz, 1H), 3.86 (d, J=11.2 Hz, 1H), 4.01 (s, 3H), 4.31 (t, J=6.7 Hz, 2H), 4.88 (d, J=10.7 Hz, 1H), 4.96 (d, J=10.7 Hz, 1H), 7.33 (m, 5H), 7.64 (s, 1H). $^{13}$C NMR (75.47 MHz, CDCl$_3$) δ 7.55, 10.41, 22.01, 31.71, 54.16, 62.95, 67.13, 70.86, 72.69, 80.12, 117.83, 122.25, 128.00, 128.42, 137.14, 144.74, 155.82, 163.16, 165.23. Nominal mass spectrum calculated m/z 403, found m/z 404 (m+1).

STEP 10A. (9CPTA→10CPTA)

9CPTA (2.13 g, 6.0 mmole) was dissolved in 1-propanol (25 mL) and DMF (50 mL) in a flask equipped with a purge line and magnetic stirring. Solid potassium carbonate (1.24 g, 9.0 mmole), palladium(II)acetate (67 mg, 0.3 mmole), and DPPP (124 mg, 0.3 mmole) were charged to the vessel which was then purged with carbon monoxide and heated to 85° C. for 15 hours. The reaction mixture was then cooled to room temperature and purged with nitrogen. The solution was filtered over celite and the celite washed with ethyl acetate (3×50 mL). The combined filtrate and washings were concentrated under vacuum to an oil. The oil was diluted with ethyl acetate (100 mL), and the resulting solution was washed with water (50 mL) and then concentrated under vacuum. The product was isolated by column chromatography (silica gel, 230–400 mesh, 1:4 ethyl acetate:hexane eluent) to yield 1.40 g (58%) 10CPT.

After STEPS 10 are performed the optical isomers may be resolved, this is referred to in the CHARTS as STEP 10 resolution, see Chart CPT p.4.

STEP 10 Resolution.

To 10CPT (8.0 g, 20 mmol) suspended in 200 mL of methyl tert-butyl ether is added 8.0 g of PS-30 catalyst (Pseudomonas cepaica lipase immobilized on equal weight of Celite 521) and 1.85 mL (20 mmol) of vinyl acetate. The resulting suspension was magnetically stirred at room temperature for 24 h. The catalyst was removed by filtration, the catalyst washed with methyl tert-butyl ether (3×100 mL), and the organic solvent concentrated under vacuum to approximately 25 mL. The solution was kept was 0–5° C., the resulting solid collected by filtration, and washed with hexane (3×25 mL) to give 2.75 g of 10CPT (s-enantiomer), $[a]_D^{25}$=+3.25° in chloroform (>99% ee HPLC Chiralpak AD column, 90:10 hexane-isopropanol, 1 ml/min, 254 nm).

STEP 11. (10CPT→11CPT)

10CPT (0.565 g, 1.4 mmole), 4-acetoxy-TEMPO (0.006 g, 0.028 mmole), potassium bromide (0.0167 g, 0.14 mmole), and sodium bicarbonate (0.0153 g, 0.182 mmole) were charged to a flask. Methylene chloride (7 mL) and water (1 mL) were added and the mixture was stirred at room temperature for 5 min. A solution of sodium hypochlorite (1.6 mL, 0.95M) was added via syringe pump over about 40 min. At the end of this addition reaction was quenched by the addition of 5% aqueous sodium metabisulfite solution. The aqueous phase was separated and extracted 2×5 mL with methylene chloride. The combined organic phases were dried over sodium sulfate and evaporated to yield 0.601 g of a brown syrup. Chemical yield essentially 100%.

$^1$H NMR (300.13 MHz, CDCl$_3$) δ 0.91 (t, J=7.5 Hz, 3H), 1.03 (t, J=7.5 Hz, 3H), 1.83 (m, 2H), 2.10 (m, 2H), 4.02 (s, 3H), 4.35 (t, J=6.6 Hz, 2H), 4.55 (s, 2H), 4.68 (d, J=11.7 Hz, 1H), 4.87 (d, J=11.7 Hz, 1H), 7.35 (m, 5H), 7.78 (s, 1H), 9.62 (s, 1H). $^{13}$C NMR (75.47 MHz, CDCl$_3$) δ 7.24, 10.43, 22.02, 29.72, 54.30, 63.2, 67.24, 73.12, 82.37, 117.45, 122.48, 128.23, 128.55, 136.67, 145.05, 150.55, 162.88, 164.93, 200.14. Nominal mass spectrum calculated m/z 401, found m/z 402 (m+1).

Alternative Reactions.

There are two different reactions routes for STEPS 12, called Pathway A or Pathway B. Pathway A has two parts. The second Part of Pathway A, Part 2, has two reaction routes, path a, a one step procedure and path b, a two step procedure. Pathway B has a total of three parts. The second intermediate produced via Pathway A, Part 2, path b-1, 12 GA-2, is the same as the second intermediate produced via Pathway B, Part 2, 12 GB-2. The third part of Pathway B is the same as the second step of Pathway A, Part 2, path b-2. See CHART CPT p. 5.

STEP 12 Pathway A, Part 1. (11CPT→12CPT A-1)

A solution of 11CPT (0.206 g, 0.5 mmole) in 6 mL of t-butanol was mixed with a solution of NaH$_2$PO$_4$ (0.035 g) in 2 mL of water and cooled to 0°. 50% hydrogen peroxide solution (0.043 mL) was added, then a solution of sodium chlorite (0.076 g, 0.675 mmole) in 0.5 mL of water was added all at once. After 5 min, the reaction was quenched by the addition of 1.8 mL of 10% aqueous sodium metabisulfite solution. The mixture was partitioned between water and methylene chloride and the aqueous phase extracted 2× with methylene chloride. The combined organic phases were evaporated to yield 0.200 g (93%) of the product 12 CPT A-1.

$^1$H NMR (300.13 MHz, CDCl$_3$) δ 1.02 (m, 6H), 1.82 (m, 2H), 2.23 (m, 2H), 3.99 (s, 3H), 4.32 (t, J=6.9 Hz, 2H), 4.53 (d, J=11.7 Hz, 1H), 4.62 (d, J=11.7 Hz, 1H), 4.68 (d, J=11.7 Hz, 1H), 4.97 (d, J=11.7 Hz, 1H), 7.32 (m, 5H), 7.90 (s, 1H). $^{13}$C NMR (75.47 MHz, CDCl$_3$) δ 7.83, 10.41, 22.01, 32.15, 54.36, 62.62, 67.31, 72.95, 79.21, 117.39, 121.82, 128.21, 128.52, 136.52, 145.25, 152.55, 162.97, 165.01, 176.06. Nominal mass spectrum calculated m/z 417, found m/z 418 (m+1).

STEP 12, Pathway A, Part 2, path a. (one step) (12 CPT A-1→12CPT)

A solution of 12A-1 CPT (0.17 g, 0.40 mmole) and pyridine (0.05 mL, 0.6 mmole) in 5 mL of acetonitrile was stirred at room temperature. Trimethylsilyliodide (0.2 mL, 1.4 mmole) was added and the mixture was stirred overnight at room temperature, then heated at 45° for 48 hours. Hydrochloric acid (5 mL, 6N) was added and the mixture was stirred at room temperature for 15 min. The mixture was extracted 3×5 mL ethyl acetate and the combined extracts were washed with 5% sodium bisulfite solution. The ethyl acetate solution was dried over sodium sulfate and evaporated. The residue was chromatographed on silica with 95:5 methylene chloride/methanol to yield 0.083 g (69%) of the product as a light yellow oil.

$^1$H NMR (300.13 MHz, CDCl$_3$) δ 1.02 (m, 6H), 1.80 (m, 4H), 4.36 (t, J=6.0 Hz, 2H), 5.22 (d, J=16.5 Hz, 1H), 5.60 (d, J=16.5 Hz, 1H), 7.40 (s, 1H). $^{13}$C NMR (75.47 MHz, CDCl$_3$) δ 7.66, 10.33, 21.84, 31.88, 66.07, 68.68, 72.32, 107.10, 124.45, 134.41, 149.99, 159.80, 173.26, 176.63. Nominal mass spectrum calculated m/z 295, found m/z 296 (m+1).

STEP 12, Pathway A, Part 2, path b-1. (12 CPT A-1→12CPT A-2)

A solution of hydroxy acid 12CPT A-l (2.64 g, 6.3 mmole) in 50 mL of methanol was stirred with 10% palladium on carbon (0.264 g) under an atmosphere of hydrogen at atmospheric pressure for 2 hours at room temperature. The catalyst was removed by filtration through celite and washed with 10 mL of methanol. The combined filtrate and washing were evaporated to yield the product (1.82 g, 93%) as a light yellow, very viscous oil.

$^1$H NMR (300.13 MHz, CDCl$_3$) δ d 0.88 (t, J=7.5 Hz, 3H), 0.97 (t, J=7.6 Hz, 3H), 1.76 (m, 4H), 4.0 (s, 3H), 4.25 (t, J=6.9 Hz, 2H), 5.23 (d, J=16.2 Hz, 1H), 5.52 (d, J=16.2 Hz, 1H), 7.85 (s, 1H). $^{13}$C NMR (75.47 MHz, CDCl$_3$) δ 7.49, 10.32, 21.89, 31.88, 54.08, 65.53, 67.22, 72.72, 114.79,115.22,146.01, 148.91, 158.50, 164.51, 173.53.

STEP 12, Pathway A, Part 2, path b-2. (12 CPT A-2→12 CPT)

A solution of hydroxylactone 12CPT A-2 (1.93 g, 6.2 mmole) and sodium iodide (1.86 g, 12.4 mmole) in 30 mL of acetonitrile was stirred at 0°. Trimethylsilyl iodide (1.6 mL, 12.4 mmole) was added and the mixture was stirred and allowed to warm to room temperature over 12 hours. Additional sodium iodide (0.9 g, 6.2 mmole) and trimethylsilyl chloride (0.8 mL, 6.2 mmole) were added and stirring was continued for 6 more hours. 1N hydrochloric acid (10 mL0 was and sodium metabisulfite (0.6 g) were added and the mixture was stirred at room temperature for 1 hour. Ethyl acetate (30 mL) was added and the aqueous phase was extracted with an additional 30 mL of ethyl acetate. The combined organic phases were washed with water, dried over sodium sulfate, and evaporated to yield the product as a light yellow solid 1.84 g, 100%).

$^1$H NMR (300.13 MHz, CDCl$_3$) δ 1.02 (m, 6H), 1.80 (m, 4H), 4.36 (t, J=6.0 Hz, 2H), 5.22 (d, J=16.5 Hz, 1H), 5.60 (d, J=16.5 Hz, 1H), 7.40 (s, 1H). $^{13}$C NMR (75.47 MHz, CDCl$_3$) δ 7.66, 10.33, 21.84, 31.88, 66.07, 68.68, 72.32, 107.10, 124.45, 134.41, 149.99, 159.80, 173.26, 176.63. Nominal mass spectrum calculated m/z 295, found m/z 296 (m+1).

STEP 12, Pathway B, Part 1. (11 CPT→12 CPT B-1)

Hydroxyaldehyde 11CPT (2.62 g, 6.6 mole) was dissolved in 30 mL of methanol and stirred with 10% palladium on carbon (0.26 g) under an atmosphere of hydrogen at atmospheric pressure. After 96 hours the reaction was complete. The catalyst was removed by filtration through celite and washed with 10 mL of methanol. The combined filtrate and washing were evaporated to yield 1.97 g (96%) of the product as a white solid.

$^1$H NMR (300.13 MHz, CDCl$_3$) δ, 0.84 (t, J=7.5 Hz, 311), 0.95 (t, J=7.4 Hz, 3H), 1.73 (m, 4H), 3.89 (s, 3H), 4.24 (t, J=6.7 Hz, 2H), 4.57 (d, J=17.2 Hz, 1H), 4.73 (d, J=17.2 Hz, 1H), 7.86 (s, 1H). $^{13}$C NMR (75.47 MHz, CDCl$_3$) δ 7.53, 10.36, 21.94, 31.70, 53.69, 58.31, 67.04, 70.68, 93.26, 116.57, 120.38, 143.54, 148.98, 158.48, 165.34.

STEP 12, Pathway B, Part 2. (12 CPT B-1→12 CPT B-2)

A solution of the lactol 12CPT B-1 (1.94 g, 6.2 mmole) in 37 mL of methylene chloride was stirred at room temperature with a solution of TEMPO (0.04 g, 0.25 mmole), sodium bicarbonate (0.081 g, 0.96 mmole), and potassium bromide (0.088 g, 0.74 mmole) in 3 mL of water. Sodium hypochlorite solution (12%, approximately 12 mL) was added dropwise over 30 min. Sodium bisulfite (1.0 g) was added to destroy the excess sodium hypochlorite. The aqueous phase was extracted with methylene chloride (10 mL) and the combined organic phases were washed once with water (10 mL) and dried over sodium sulfate. The solvent was evaporated to yield the product (1.90 g, 99%) as an oil that solidified on standing.

$^1$H NMR (300.13 MHz, CDCl$_3$) δ d 0.88 (t, J=7.5 Hz, 3H), 0.97 (t, J=7.6 Hz, 3H), 1.76 (m, 4H), 4.0 (s, 3H), 4.25 (t, J=6.9 Hz, 2H), 5.23 (d, J=16.2 Hz, 1H), 5.52 (d, J=16.2 Hz, 1H), 7.85 (s, 1H). $^{13}$C NMR (75.47 MHz, CDCl$_3$) δ 7.49, 10.32, 21.89, 31.88, 54.08, 65.53, 67.22, 72.72, 114.79, 115.22, 146.01, 148.91, 158.50, 164.51, 173.53. Nominal mass spectrum calculated m/z , found m/z.

STEP 12, Pathway B, Part 3. (12 CPT B-2→12 CPT)

This step is identical to, and the procedures used are the same as, STEP 12. STEP 13, Pathway A, Part 2, path b-2. (12 CPT→13 CPT)

12CPT (10.1 g, 0.339 mole), cesium carbonate (22.0 g, 0.067 mole), t-butyl acrylate (25 mL, 0.169 mole), and DMSO (150 mL) were stirred at 47–50° for 19 hours. The mixture was cooled and 20 mL of concd hydrochloric acid and 180 mL of water were added. The mixture was extracted 4 times with a total of 500 mL of a 4:1 (v/v) mixture of toluene and ethyl acetate. The combined extracts were washed three times with water and then evaporated to an oil. 200 mL of toluene was added and the solution was concentrated to yield 13CPT solvate, as the crystalline 1:1 toluene solvate (11.5 g, 67%).

$^1$H NMR (300.13 MHz, CDCl$_3$) δ 0.92 (t, J=7.4 Hz, 3H), 1.50 (s, 9H), 1.71–1.79 (m, 2H), 2.28 (s, 3H), 4.59 (s, 2H), 5.16 (d, J=17.8 Hz, 1H), 5.61 (d, J=17.8 Hz, 1H), 6.94 (s, 1H), 7.0–7.2 (m, 5H). $^{13}$C NMR (75.47 MHz, CDCl$_3$) δ 7.64, 21.38, 28.20, 31.41, 49.27, 66.13, 72.50, 83.55, 97.80, 105.69, 118.59, 125.22, 128.14, 128.95, 137.78, 143.82, 149.48, 156.84, 159.26, 166.02, 173.60.

STEP 14. (13 CPT→14 CPT)

The 13CPT-toluene solvate (70.3 g, 0.153 mole) was dissolved in 1400 mL toluene and 140mL trifluoroacetic acid and heated at 110° for 2 hours. The solution was cooled and concentrated under vacuum to about 350 mL. Ethyl acetate (1L) was added and the mixture was cooled to −20°. Filtration yielded 14 CPT as a light brown crystalline solid (37.92 g, 93.4%).

$^1$H NMR (300.13 MHz, CDCl$_3$) δ 0.98 (t, J=7.5 Hz, 3H), 1.80 (q, J=6.0 Hz, 2H), 2.96 (m, 2H), 4.36 (t, J=6 Hz, 2H), 5.24 (d, J=15 Hz, 1H), 5.66 (d, J=15 Hz, 1H), 7.2 (s, 1H). $^1$H NMR (300.13 MHz, DMSO-d$_6$) d 0.80 (t, J=7.3 Hz, 3H), 1.81 (m, 2H), 2.89 (t, J=6.3 Hz, 2H), 4.13 (t, J=6.3 Hz, 2H), 5.34 (d, J=17.1 Hz, 1H), 5.41 (d, J=17.1 Hz, 1H), 6.86 (s, 1H). $^{13}$C NMR (75.47 MHz, DMSO-d$_6$) δ 7.52, 30.31, 33.71, 42.56, 65.20, 71.92, 98.49, 123.81, 140.19, 149.05, 156.97, 172.03, 197.93. Nominal mass spectrum calculated m/z 263, found m/z 264 (m+1).

ADDITIONAL DISCLOSED REACTIONS

The following reactions, procedures and formula in the Chart below are also included with this invention.

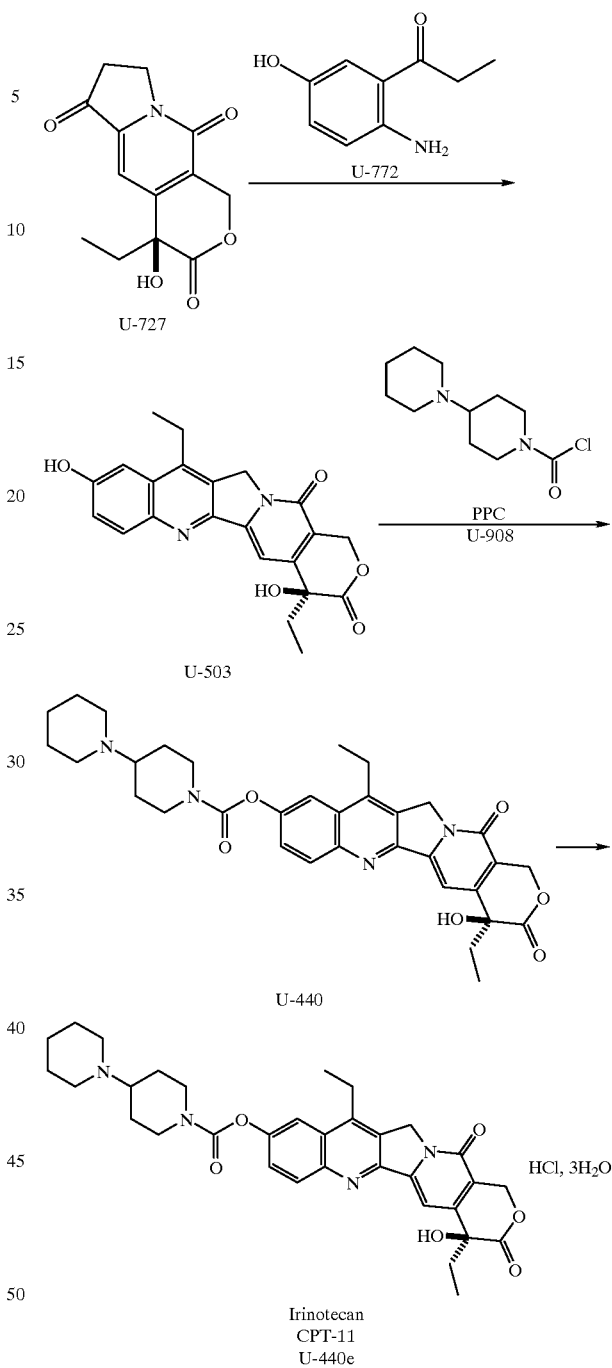

The following references may be useful in understanding the ADDITIONAL DISCLOSED REACTIONS above. The preparation of u-503 from natural camptothecin is described in U.S. Pat. No. 4,473,692 (Sep. 25, 1984), T. Miyasaka, S. Sawada, K. Nokata, M. Mutai. A related preparation of U-440 from U-503 is described in U.S. Pat. No. 4,604,463, (Aug. 5, 1986), T. Miyasaka, S. Sawada, K. Nokata, E. Siguno, M. Mutai. The conversion of U-440 into CPT-11 is described in: S. Sawada, S. Okajima, R. Aiyama, K. Nokata, T. Furuta, T. Yokohura, E. Siguno, K. Yamaguchi, T. Miyasaka, Chem. Pharm. Bull, 1991, Volume 39, pp. 1446–1454.

The reactions shown in the Additional Disclosed Reaction Chart above are described below.

Preparation of U-503 and U-440

U-727 and U-772 are reacted at 95° to 100° in a mixture of toluene and acetic acid for about 18–24 hours. The toluene and acetic are removed by distillation to yield U-503 which is converted without purification into U-440.

The unpurified U-503 is dissolved in pyridine and reacted at 20° to 25° with 4-piperidinopiperidinecarbamyl chloride dissolved in methylene chloride. The methylene chloride and pyridine are removed by distillation and the crude U-440 is redissolved in methylene chloride and treated with saturated aqueous sodium bicarbonate solution. The U-440 is then chromatographed on silica gel eluting with a mixture of methylene chloride and methanol, and isolated as a crystalline solid by crystallization from a mixture of methylene chloride and ethanol.

U-503. U-727 (1.05 g, 4.0 mmole), U-772 (0.62 g, 3.8 mmole), and p-toluenesulfonic acid monohydrate (0.02 g) are mixed with toluene (10 mL) and acetic acid (10 mL) and heated for 18–24 hours at 95° to 100°. U-503 gradually precipitates during the course of the reaction. When the reaction is complete the toluene and acetic acid are removed by distillation under reduced pressure to yield U-503 as a solid mass.

U-440. Pyridine (15 mL) is added to the unpurified U-503 and the mixture is stirred for 15 minutes at 20° to 25° to dissolve the U-503. A solution of 4-piperidinopiperidinecarbamyl chloride (1.32 g, 5.7 mmole) dissolved in methylene chloride (5 mL) is added. The mixture is stirred at 20–25° for 2 hours to complete the reaction. The mixture is distilled to dryness under reduced pressure. Toluene (20 mL) is added and the mixture is distilled to near dryness under reduced pressure.

The unpurified U440 is dissolved in methylene chloride (25 mL), saturated aqueous sodium bicarbonate solution (5 mL) is added, and the mixture is stirred at room temperature for 5 min. The phases are allowed to settle and the methylene chloride phase is removed. The aqueous phase is extracted with with methylene chloride (10 mL). The methylene chloride phases are combined and distilled to yield crude solid U-440.

The crude solid U-440 is dissolved in 95:5 methylene chloride-methanol (v/v, 10 mL) and chromatographed on a column packed with 30 g of 230–400 mesh silica, eluting with and 95:5 methylene chloride-methanol (v/v). The product containing fractions are combined and distilled to a volume of about 10 mL under atmospheric pressure. Some product crystallization may occur at the end of the distillation. Ethanol (15 mL) is added and the slurry is allowed to stand at −20° C. for 24 hours. The product is filtered, washed with ethanol (10 mL), and dried to yield 1.34 g (62% chemical from 16CPT) of U-140.

PROCEDURES, REACTIONS AND COMPOUNDS OF CHART M-M and M-G

Chiral Reduction for Mappicine Synthesis and related compounds shown in CHARTS M-G and M-M. The precursors of these compounds are described by the early reactions of CHART G.

There are a number of reagents available for the reduction of ketones to produce chiral secondary alcohols. Aryl-alkyl ketones similar in structure to the intermediates shown in the mappicine CHARTS are particularly favorable substrates for chiral reduction. Among the reagents that are effective for this type of reduction are Noyori's binaphthol-lithium aluminum hydride complex[1], complexes of borane and chiral amino alcohols developed by Itsuno[2], borane reductions catalyzed by chiral oxazaborolidines[3], and complexes of lithium aluminum hydride and darvon alcohol[4].

1. R. Noyori, I. Tomino, and Y. Tanimoto, *J. Am. Chem. Soc*, 1979, 101, 3129; R. Noyori, U.S. Pat. No. 4,284,581.
2. S. Itsuno, K. Ito, A. Hirao, and S. Nakahama, *J. Chem. Soc. Chem. Comm.*, 1983, 469; S. Itsuno, M. Nakano, K. Miyazaki, H.Masuda, K. Ito, A. Hirao, and S. Nakahama, *J. Chem. Soc. Perkin* I, 1985, 2039.
3. E. J. Corey, R. K. Bakshi, S. Shibate, *J. Am. Chem. Soc.* 1987, 5551.
4. N. Cohen, R. J. Lopresti, C. Neukom, G. Saucey, *J. Org. Chem.* 1980, 45, 582.

Reaction products and intermediate from the above can then be reacted in obvious variants of the Friedlander type condensation to produce desired products such as those shown in the CHARTS below.

The following is one specific example showing, in detail, the conditions for the reactions shown in CHARTS M-G and M-M.

5MM. 4CPT (10.0 g, 41.0 mmol) was dissolved in 500 mL of heptane. The solution was cooled to 0° C. and 24.4 mL of n-BuLi in hexanes (2.10M, 51.2 mmol) was added while maintaining reaction temperature at 0° C. The bright-orange slurry was stirred at 0° C. for 1.75 h. Dimethyl sulfate (4.8 mL, 51.2 mmol) was added maintaining reaction temperature below 10° C. The reaction was stirred at 0° C. for 2 h, and then treated with 1.5 mL of conc. $NH_4OH$ before stirring an additional 1 h. Water (40 mL) and EtOAc (75 mL) were added. After 15 min, the phases were partitioned and the aqueous extracted from with 3×50 mL portions of EtOAc. The organic extracts were combined, dried over $Na_2SO_4$, filtered and concentrated to a red oil. Purification by flash-chromatography ($CH_2Cl_2$) gave 5MM (6.97 g, 66%) as a clear, colorless oil: MS (EI) m/z 257, 259; MS (CI) m/z (—$NH_3^+$) 258, 260; $^1H$ NMR (300.14 MHz, $CDCl_3$) δ 7.08 (s, 1H), 4.05–4.01 (m, 2H), 3.97 (s, 3H), 3.80–3.75 (m, 2H), 2.28 (s, 3H), 1.93 (dd, J=7.4, 14.9 Hz), 0.91 (t, J=7.4 Hz); $^{13}C$ NMR (75.47 MHz) δ 162.9, 153.3, 144.9, 116.9, 114.4, 110.1, 64.5, 54.2, 31.5, 12.0, 7.4.

6MM. 5MM (12.0 g, 46 mmol) was dissolved in 25 mL of aqueous TFA (64% v/v) and heated to 40° C. After 4 h, the reaction mixture was cooled and quenched with 50 mL $H_2O$ and 75 mL 2:1 (v/v) EtOAc:heptane. The phases were partitioned and the aqueous extracted from with 3×40 mL portions of 2:1 EtOAc:heptane. The organic extracts were combined and neutralized by washing with 200 mL of 9% (w/v) aqueous $NaHCO_3$. The phases were partitioned and the aqueous phase was extracted from with 3×50 mL portions of EtOAc. The organic phases were combined, dried ($Na_2SO_4$), filtered and concentrated to give 10 g of a yellowish oil. The crude product was carried directly into the next reaction. A small portion was purified for characterization: MS (EI) m/z 213, 215; MS (CI) m/z (—$NH_3^+$) 214, 216; $^1H$ NMR (300.14 MHz, CDCl3) δ 0.88 (s, 1H), 3.99 (s, 3H), 2.82 (dd, J=7.2, 14.5 Hz), 2.16 (s, 3H), 1.19 (t, J=7.2 Hz); $^{13}C$ NMR (75.47 MHz) δ 204.2, 162.6, 150.5, 145.5, 116.3, 113.0, 54.4, 35.9, 11.8, 7.6.

6bMM. Crude 6MM (10 g, approx 46 mmol) was dissolved in 100 mL of MeOH and cooled to 0° C. A freshly-prepared solution of 2.18 g of $NaBH_4$ (58 mmol) in 20 mL of 50% aqueous MeOH was added in all at once. After 20 min, the reaction was quenched with 50 mL aqueous HCl (1M, 50 mmol) and then diluted with 100 mL $CH_2Cl_2$ and 10 mL of water. The phases were partitioned and the aqueous phase was extracted with 3×50 mL portions of $CH_2Cl_2$. The organic extracts were concentrated to a white solid. The solid material was recrystallized from hexane to give 7MM (8.54 g, 85% from 5MM) as long needles: mp=97.0–97.5° C.; MS (EI) m/z 215, 217; MS (CI) m/z (—$NH_3^+$) 216, 218; $^1H$ NMR (300.14 MHz, $CDCl_3$) δ 7.05 (s, 1H), 4.85–4.81 (m, 1H), 3.95 (s, 3H), 2.08 (s, 3H), 1.76–1.63 (m, 2H), 0.98 (t, J=7.4 Hz); $^{13}C$ NMR (75.47 MHz) δ 161.8, 155.6, 145.4, 115.0, 113.1, 71.0, 54.1, 30.4, 10.5, 9.8.

7MM 7MM (4.00, 18.5 mmol) and sodium hydride (1.55 g, 64.6 mmol) were stirred with 40 mL of THF for 30 min. Benzyl bromide (2.3 mL, 18.9 mmol) was added and the mixture was stirred for 8 hours at room temperature. Saturate ammonium chloride solution (10 mL), 10 mL of water, and 20 mL $CH_2Cl_2$ were added. The phases were partitioned and the pH of the aqueous phase was adjusted with 1M HCl to neutrality before extracting with 3×20 mL portions of $CH_2Cl_2$. The organic phases were combined, dried ($Na_2SO_4$), filtered and concentrated to a yellow oil. Flash chromatography over silica gel gave 8MM (5.09 g, 90%) as a clear oil: MS (EI) m/z 305, 307; MS (CI) m/z ($—NH_3^+$) 306, 308; $^1$H NMR (300.14 MHz, $CDCl_3$) δ 7.38–7.32 (m, 5H), 7.07 (s, 1H), 4.53–4.46 (m, 2H), 4.26 (d, J=11.7 Hz, 1H), 4.00 (s, 3H), 2.09 (s, 3H), 1.83–1.62 (m, 1H), 0.98 (t, J=7.3 Hz, 3H); $^{13}$C NMR (75.47 MHz) δ 162.0, 154.0, 145.6, 137.9, 128.4, 127.8, 127.7, 116.3, 113.8, 78.0, 71.0, 54.2, 29.5, 10.5, 10.1.

8MM 8MM (4.00 g, 13.1 mmol), potassium acetate (1.92 g, 19.6 mmol), palladium acetate (0. 147 g, 0.65 mmol), and DPPP (0.268 g, 0.65 mmol), were stirred with 80 mL of DMF and 40 mL of n-propanol. The flask was purged with CO and then heated to 85° C. under an atmospherre of CO. After 25 the mixture was cooled and purged with nitrogen. The solution was filtered over celite and the filtrate was concentrated and then partitioned between 80 mL of water and 160 mL MTBE. The aqueous phase was further extracted with 3×50 mL portions of MTBE. The organic extracts were combined, washed with 4×25 mL portions of water, dried ($Na_2SO_4$), filtered and concentrated. Purification by flash chromatography using $CH_2Cl_2$ as eluent gave 9MM (4.14 g, 89%) as a clear, colorless oil: MS (EI) m/z 358; MS (CI) m/z ($—NH_3^+$) 358, 360; $^1$H NMR (300.14 MHz, $CDCl_3$) δ 7.88 (s, 1H), 7.38–7.28 (m, 5H), 4.57–4.53 (m, 1H), 4.48 (d, J=11.6 Hz, 1H), 4.36–4.32 (m, 2H), 4.25 (d,J=11.6 Hz, 1H), 4.09 (s, 3H), 2.18 (s, 3H), 1.90–1.80 (m, 3H), 1.78–1.64 (m, 2H), 1.06 (t, J=7.4 Hz), 0.97 (t, J=7.4 Hz); $^{13}$C NMR (75.47 MHz) δ 165.5, 162.3, 151.5, 142.8, 138.0, 128.3, 127.8, 127.7, 122.9, 116.5, 78.1, 70.9, 66.8, 53.8, 29.5, 22.0, 11.3, 10.4, 10.2.

9MM. A solution of sodium iodide (1.89 g, 12.6 mmol) and 8MM (3.00 g, 8.4 mmol) in 30 mL of $CH_3CN$ was cooled to 0° C. and trimethylsilyl chloride (1.6 mL, 12.6 mmol) was added. After 15 min. the reaction mixture was allowed to warm to room temperature. After 24 h the reaction was quenched by sequentially adding 4.2 mL of 6M HCl, 5.3 mL saturated sodium chloride solution, 10.6 mL $H_2O$, 0.4 mL 38% $Na_2S_2O_5$(aq) and 20 mL EtOAc. After stirring at room temperature for 30 min, the phases were separated and the aqueous phase extracted with 3×10 mL portions of EtOAc. The organic solutions were combined and washed with 7 mL of satd. $NaHCO_3$ and 0.25 mL of 38% aqueous sodium bisulfite. After stirring for 15 min, the phases were separated and the organic solution was washed with 2×10 mL of saturated aqueous sodium chloride solution. The solution was dried over $Na_2SO_4$, then filtered and concentrated to give 2.80 g (97%) of 9MM as a waxy yellow-white solid: MS (EI) m/z 343, 344; MS (CI) m/z ($—NH_3^+$) 344, 345; $^1$H NMR (300.14 MHz, $CDCl_3$) δ 9.82 (broad s), 7.39–7.29 (m, 6H), 4.51–4.46 (m, 1H), 4.35–4.26 (m, 2H), 2.14 (s, 3H), 1.87–1.75 (m, 3H), 1.71–1.57 (m, 1H), 1.05–0.95 (m, 6H); $^{13}$C NMR (75.47 MHz) δ 162.42, 161.28, 150.41, 137.63, 133.04, 130.54, 128.40, 127.87, 108.01, 77.76, 71.13, 67.95, 28.80, 21.84, 12.04, 10.29, 10.06.

10MM. A mixture of 9MM (3.22 g, 9.4 mmol), cesium carbonate (6.12 g, 18.8 mmol), t-butyl acrylate (13.5 mL, 92.3 mmol), and 50 mL of DMSO was heated to 65° C. under a nitrogen atmosphere. After 3 hours the reaction mixture was cooled to 0° C. and then slowly quenched with 60 mL of 0.5 M HCl, maintaining throughout an internal reaction temperature at or below 15° C. The mixture was diluted with 30 mL 1:4 EtOAc:toluene (v/v) and partitioned. The aqueous was extracted from with 2×30 mL portions of the above solvent. The organic extracts were combined and washed with 3×30 mL portions of water, dried over $Na_2SO_4$, filtered and concentrated to 4.57 g of yellow oil. Purification by column chromatography yields 3.28 g of 10MM as a foamy off-white solid (85%): MS (EI) m/z 411, 412; MS (CI) m/z ($—NH_3^+$) 412, 413; $^1$H NMR (300.14 MHz, $CDCl_3$) δ 9.91 (br s), 7.39–7.29 (m, 5H), 6.91 (s, 1H), 4.67 (s, 2H), 4.52–4.48 (m, 2H), 4.26 (d, J=11.8 Hz, 1H), 2.18 (s, 3H), 1.87–1.78 (m, 1H), 1.73–1.53 (m, 2H ), 1.59 (s, 9H), 0.97 (t, J=7.4 Hz, 3H); $^{13}$C NMR (75.47 MHz) δ 166.61, 160.77, 160.28, 150.69, 140.25, 137.89, 128.35, 127.77, 127.69, 126.63, 103.99, 99.13, 82.95, 78.02, 70.88, 49.08, 29.01, 28.25, 27.87, 11.84, 10.07.

11MM. A solution of 10MM (0.25 g, 0.61 mmol), trifluoroacetic acid (0.45 mL), and toluene (18 mL) was heated to 75° C. After 24 h, the solution was concentrated via rotary evaporation to a thick oil. The oil was diluted with 20 mL of toluene and concentrated to a thick oil. The oil was purified by flash chromatography (5% MeOH in $CH_2Cl_2$) to yield 0.138 g of 11MM as a foamy yellow solid (73%): MS (EI) m/z ; MS (CI) m/z ($—NH_3^+$); $^1$H NMR (300.14 MHz, $CDCl_3$) δ 7.27–7.18 (m, 5H), 7.04 (s, 1H), 4.43–4.38 (m, 2H), 4.23–4.13 (m, 3H), 2.80 (t, J=6.9 Hz), 2.09 (s, 3H), 1.75–1.47 (m, 2H), 0.86 (t, J=7.4 Hz, 3H); $^{13}$C NMR (75.47 MHz) δ 196.91, 161.48, 150.48, 137.67, 136.95, 132.94, 128.36, 127.71, 102.40, 77.77, 70.97, 41.92, 33.69, 28.90, 12.41, 9.98.

12MM. A solution of 11MM (0.135 g, 0.43 mmol), N-Boc o-aminobenzaldehyde (0.14 g, 0.63 mmol), p-toluenesulfonic acid (0.010 g, 0.06 mmol), glacial acetic acid (5 mL), and toluene (25 mL) was heated to 100° C. After 36 h the solution was concentrated under vacuum to dryness. The residue was dissolved in 25 mL of toluene and then concentrated to 0.333 g of red-brown solids. The material was purified by flash chromatography (2% MeOH in $CH_2Cl_2$) to deliver 0.123 g of 12MM as a foamy yellow solid (72%): MS (EI) m/z 396, 398; MS (CI) m/z ($—NH_3^+$) 397, 399; $^1$H NMR (300.14 MHz, $CDCl_3$) δ 8.33 (s, 1H), 8.22 (d, J=8.5 Hz, 1H), 7.90 (d, J=8.1 Hz, 1H), 7.80 (t, J=7 Hz, 1H), 7.64–7.57 (m, 2H), 7.38–7.29 (m, 5H), 5.28 (s, 2H), 4.64–4.54 (m, 2H), 4.32 (d, J=12 Hz, 1H), 2.25 (s, 3H), 1.99–1.67 (m, 1H), 1.02 (t, J=7.3 Hz); $^{13}$C NMR (75.47 MHz) δ 161.51, 153.51, 151.30, 148.78, 142.67, 138.12, 130.67, 130.12, 129.56, 128.64, 128.33, 127.98, 127.76, 127.60, 127.29, 126.87, 99.51, 78.18, 70.81, 49.91, 29.08, 11.99, 10.19.

CHARTS

Charts useful in the description of this invention are described briefly here and appear on the following pages. Detailed description is provided above. CHART G is a general description showing the generic structures involved in the reactions. After the production of the compound labeled 4G there are two quite different reaction pathways that may be pursued. One pathway continues with CHART G and eventually results in the production of camptothecin or related compounds. The other pathway, CHART M-G, eventually results in the production of mappicine or related compounds.

CHART CPT-11 is one species specific embodiment of CHART G that shows the specific reactions and intermediates resulting in the production of camptothecin. CHART M-M is one species specific embodiment of CHART M that shows the specific reactions and intermediates resulting in the production of mappicine.

Step 10 in CHARTS G and CPT-11 show the resolution of enantiomers. Although only one enantiomer is shown, the other enantiomer could also be resolved using appropriate starting materials and making the necessary modifications that would be obvious to one of ordinary skill in the art. The procedures would then be applicable to whatever enantiomer or mixtures of enantiomers, was desired.

When only one asymmetric center is present, the procedures, with appropriate modifications as needed, may be used to produce either enantiomer. When two asymmetric centers are present, the sterochemistry of only one of the two centers may be shown. When there are two asymmetric centers in a molecule, the procedures herein will generally result in resolution of only one asymetric center, the second center will usually be unresolved. By making appropriate modifications to the procedures herein in combination with procedures available to one ordinarily skilled in the art, complete resolution of all four stercoisomers could be accomplished for the molecules having two asymmetric centers.

CHARTS M-G and G-G show one enantiomer, with a bold line showing orientation, however; the other enantiomer could just as well be made and isolated using procedures known to one ordinarily skilled in the art. The procedures would then be applicable to whatever enantiomer, or mixtures of enantiomers, was selected. The other enantiomers from CHARTS M-G and G-G are shown in some of the claims where the orientation is shown with either a bold or a dotted line.

Hydrogen atoms, and their connecting bonds, are not usually shown in the following CHARTS or in any of the formula used herein. Sometimes carbon atoms are only indicated by bonds and not by the letter "c."

The various charts follow.

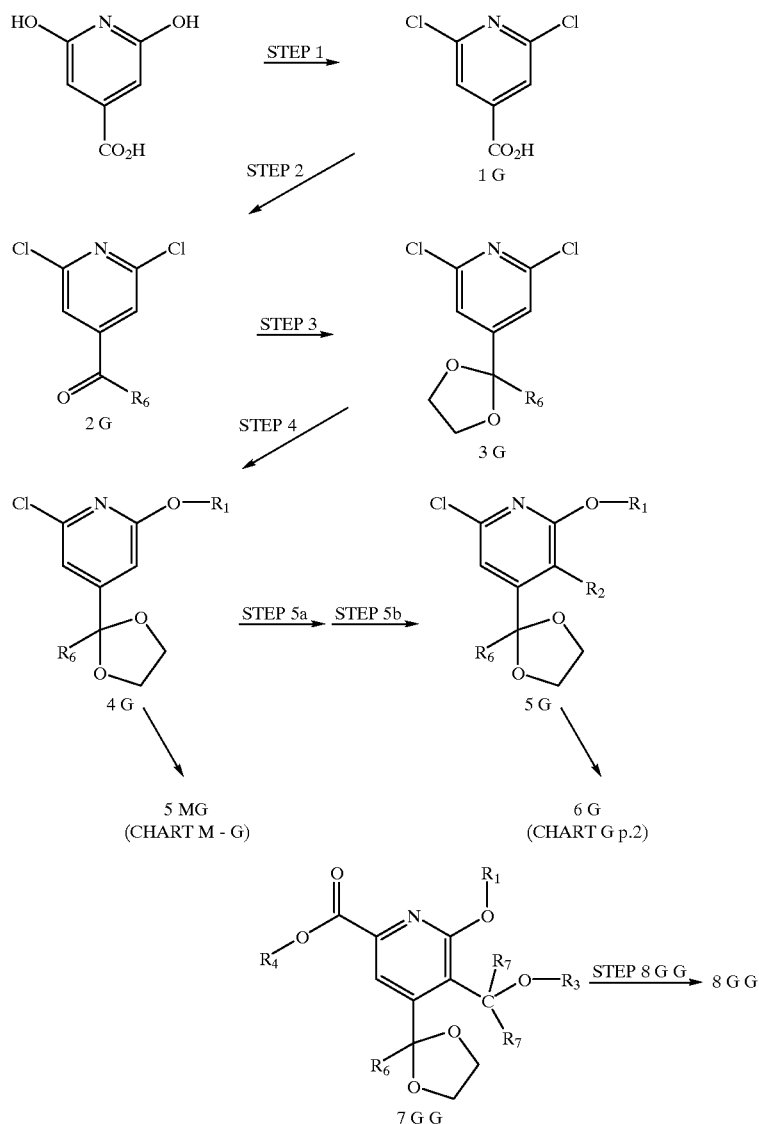

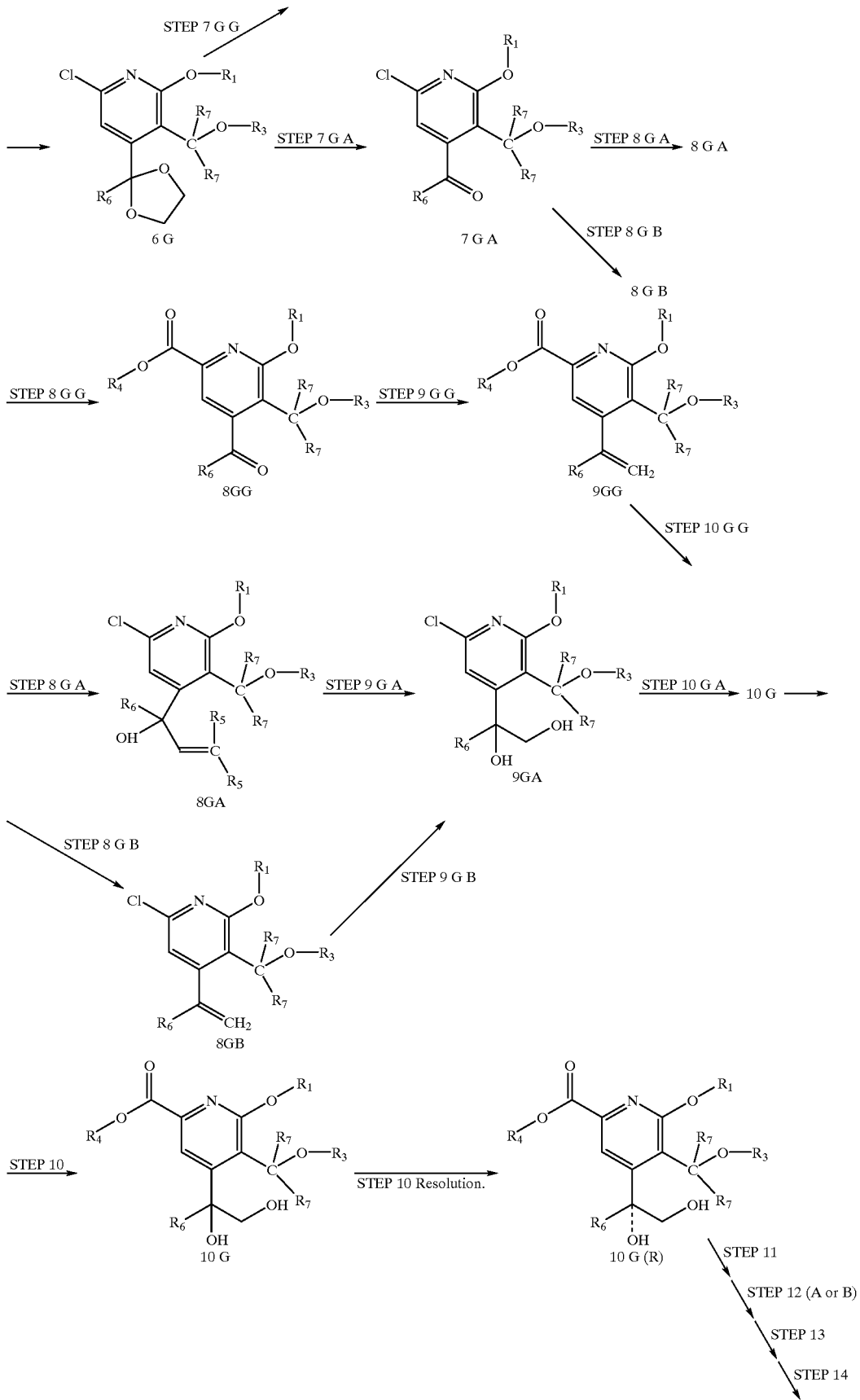

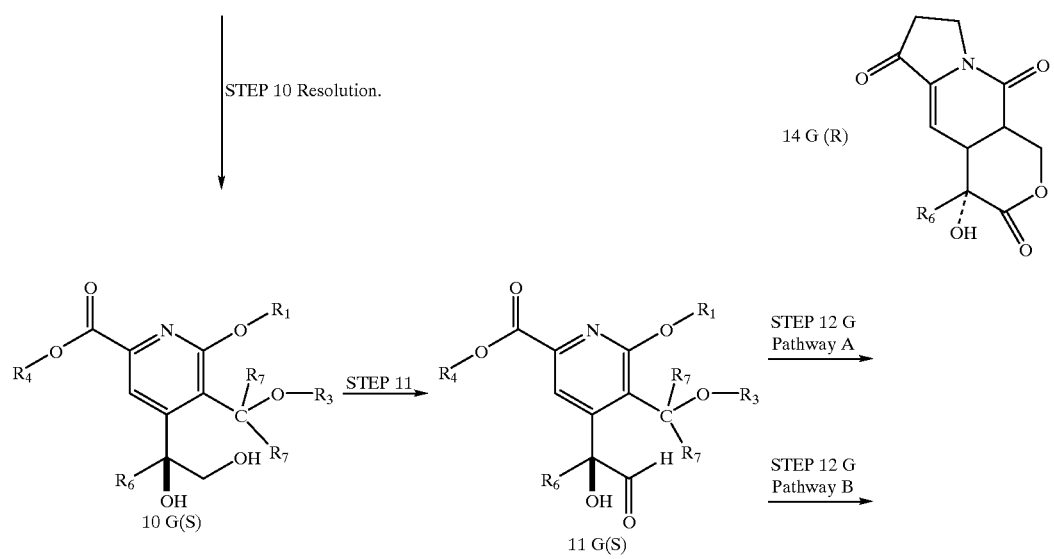
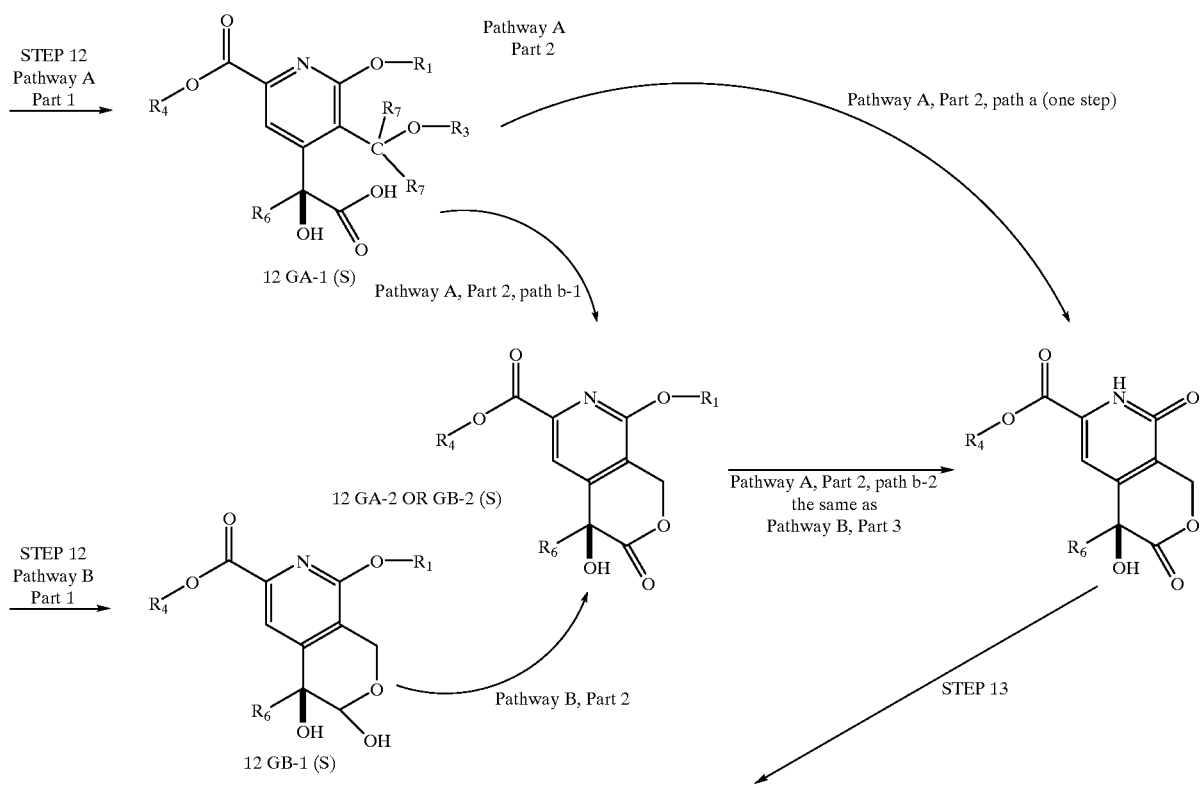
CHART G p.5

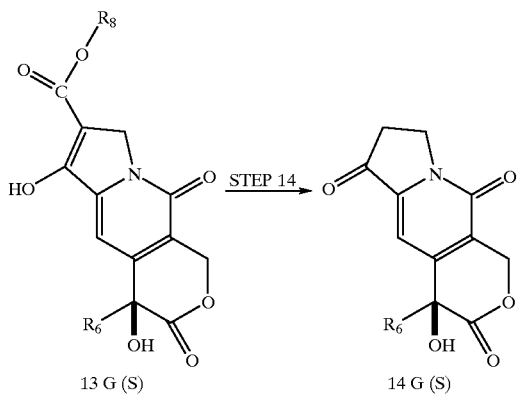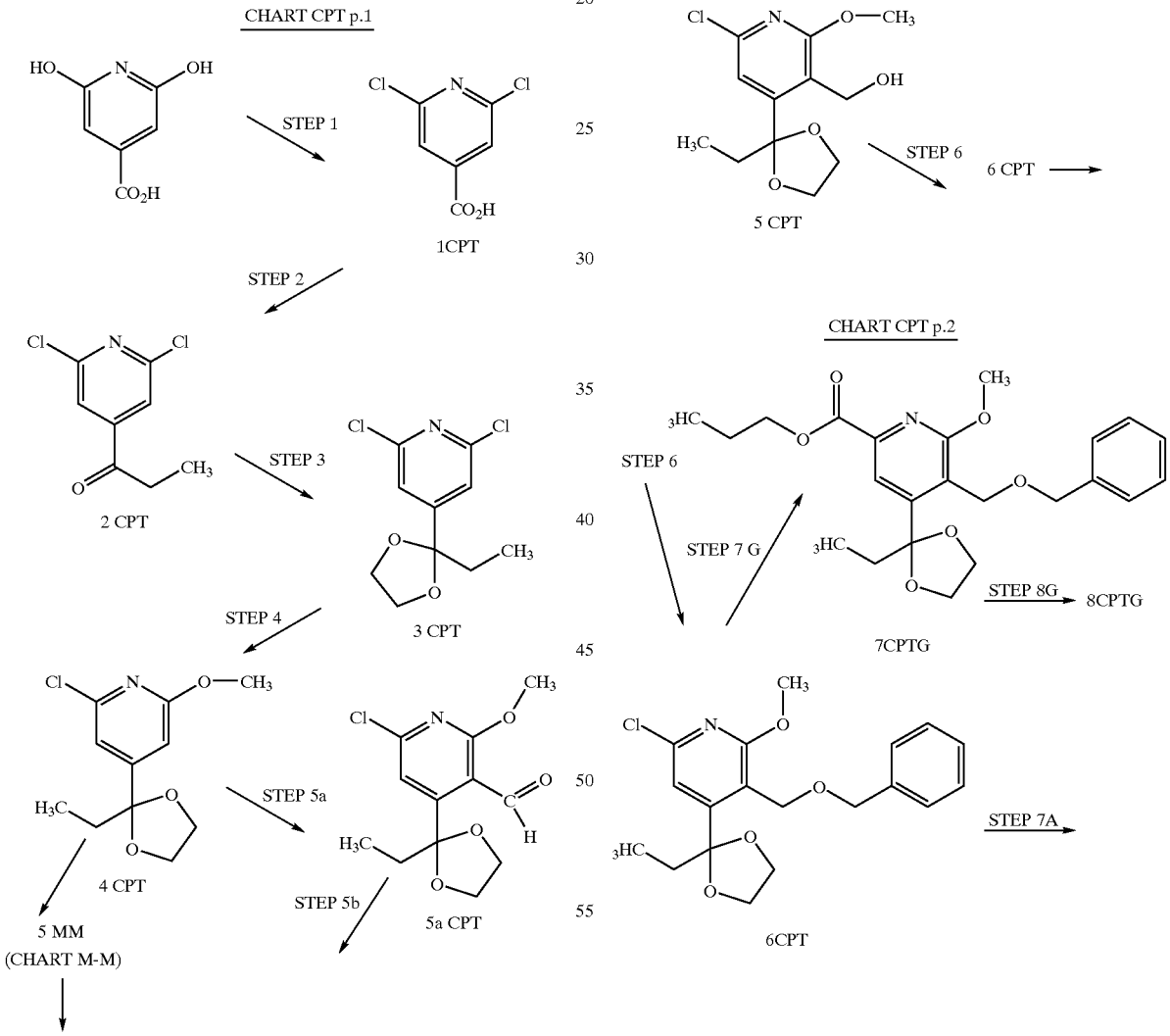

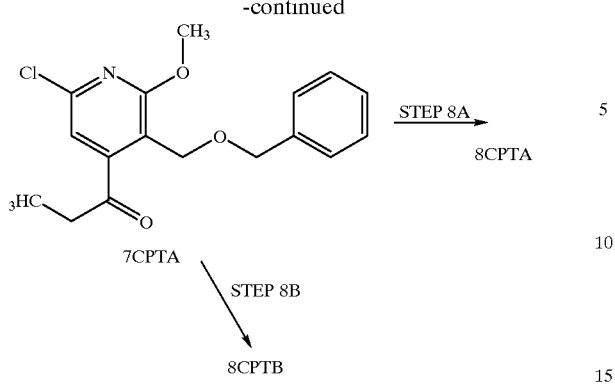
CHART CPT p.3
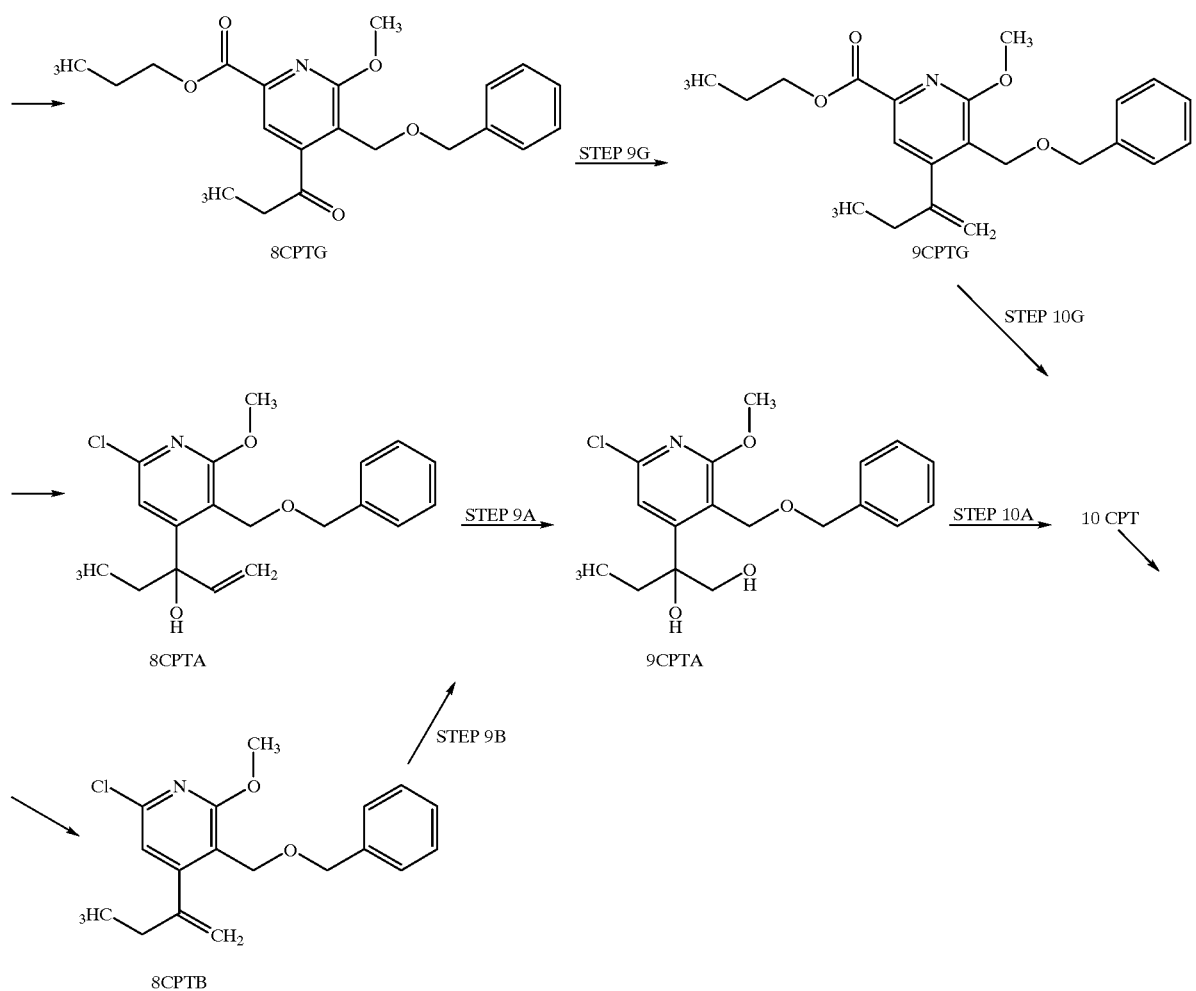

CHART CPT p.4
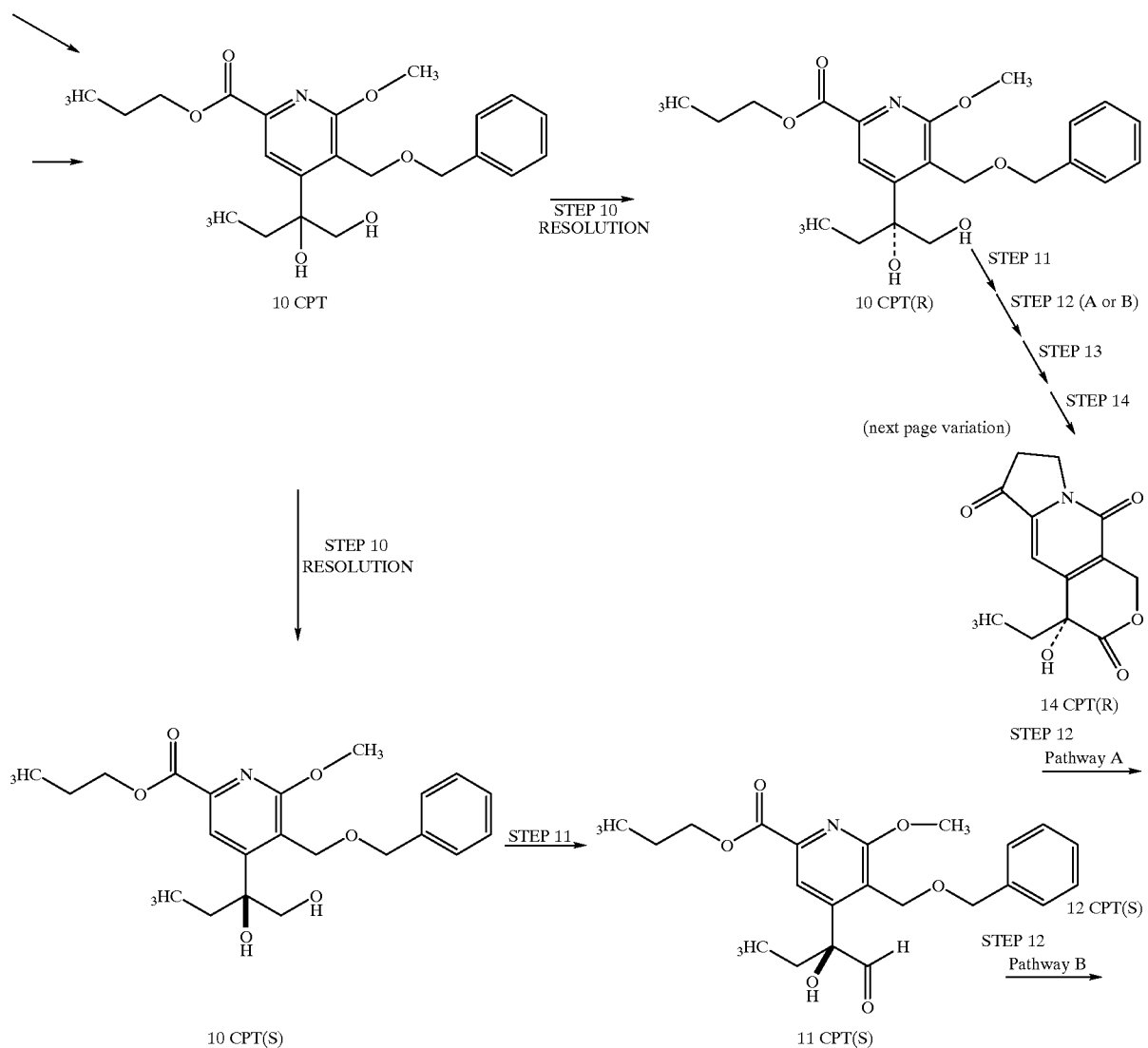

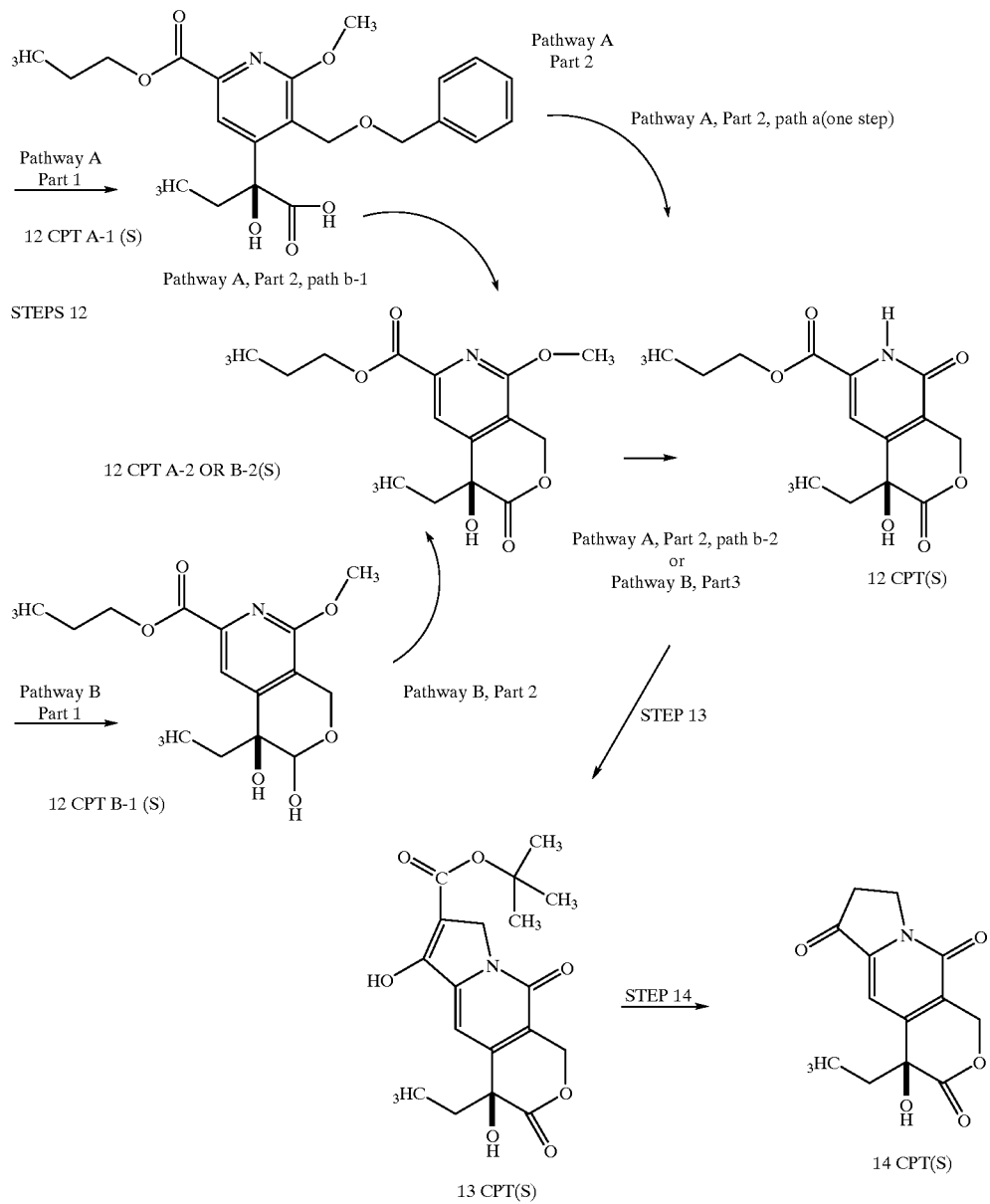
CHART CPT p.5
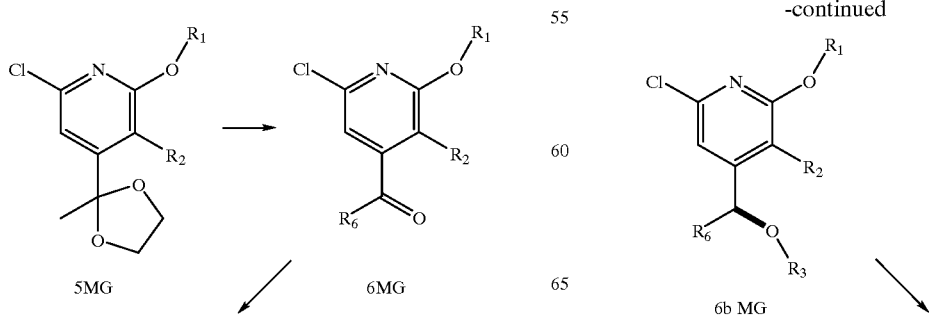
CHART M-G p.1

41
-continued
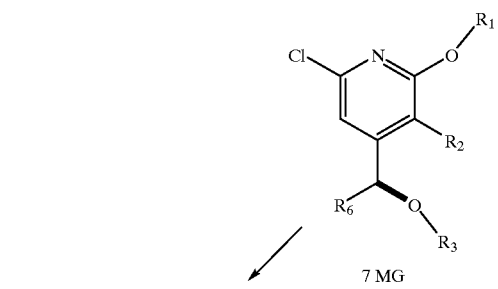
7 MG
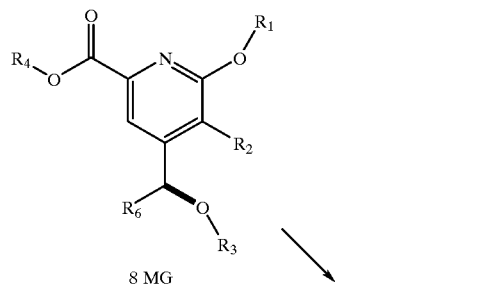
8 MG
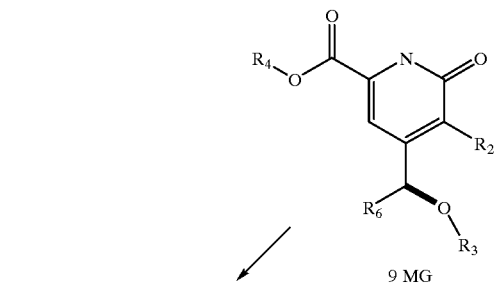
9 MG
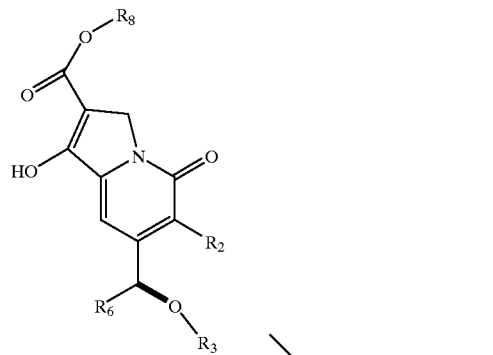
10 MG
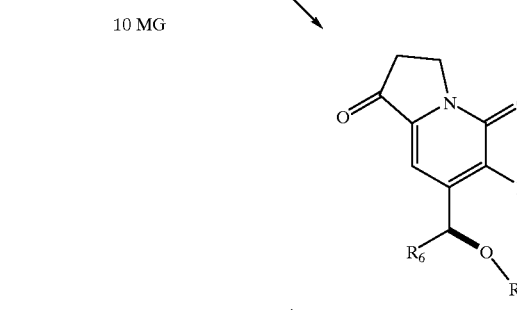
11 MG
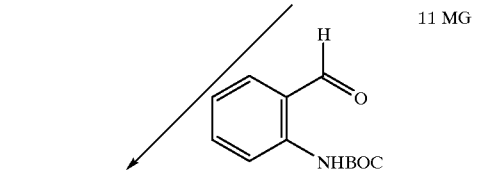
42
-continued
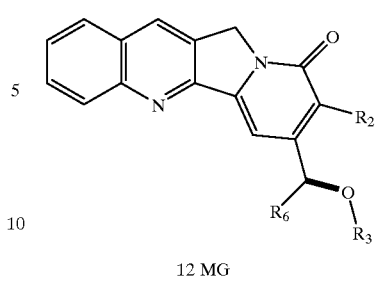
12 MG
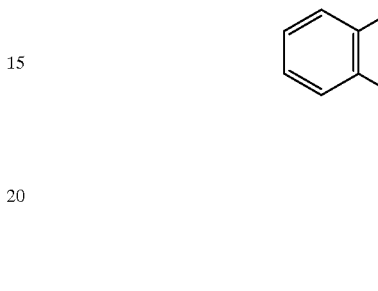
13 MG
CHART M-M p.1
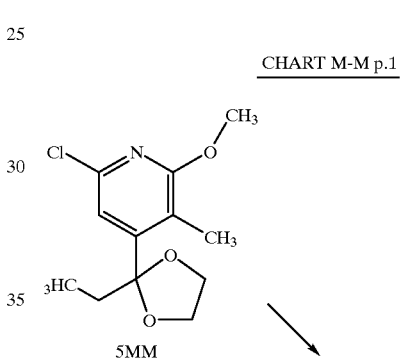
5MM
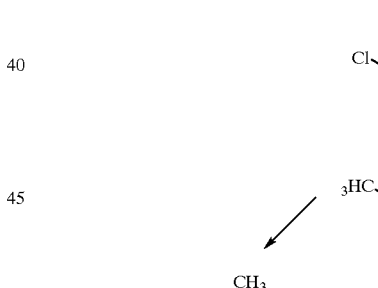
6MM
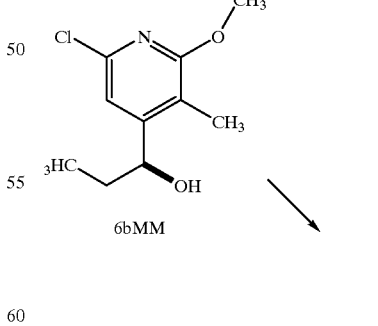
6bMM

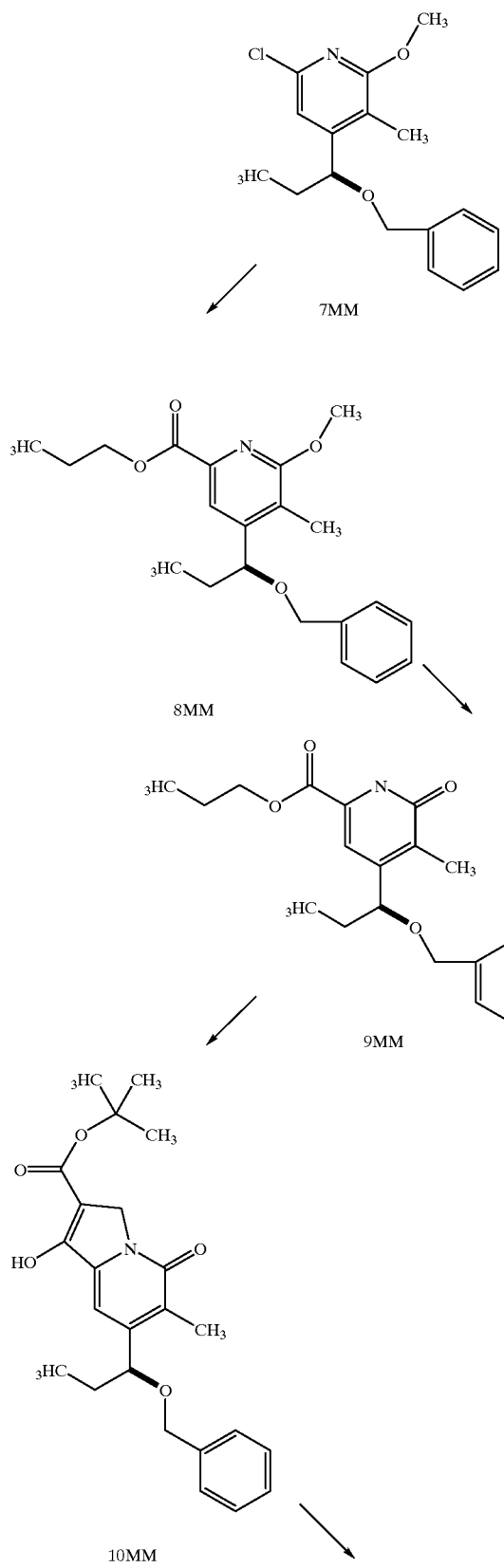
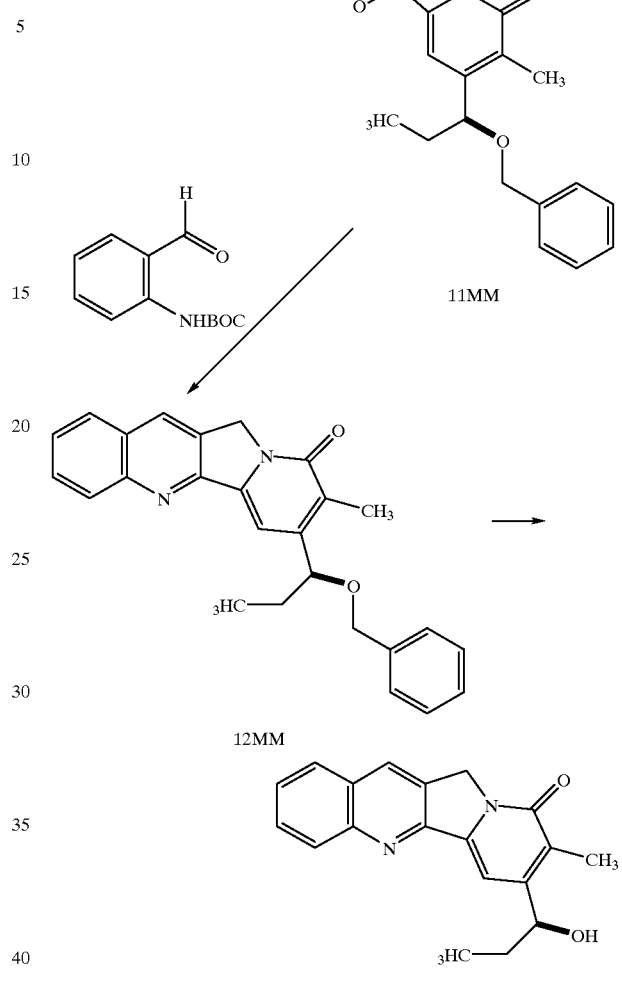

What is claimed is:

1. The process for producing the compounds described and labeled in the specification as of formula 13G comprising the step of mixing the compounds described and labeled in the specification as of formula 12G with an acrylate ester in the presence of base; wherein $R_4$ is optionally substituted $C_{1-8}$ alkyl, $C_{3-10}$ cycloalkyl, lower alkyl-$C_{3-10}$ cycloalkyl, alkenyl, aryl, substituted aryl, alkylaryl, or substituted alkylaryl;

$R_6$ is optionally substituted $C_{1-8}$ alkyl, aryl, substituted aryl, alkylaryl, substituted alkylaryl, $C_{3-10}$ cycloalkyl, lower alkyl-$C_{3-10}$ cycloalkyl, heteroaryl, or substituted heteroaryl; and $R_8$ is optionally substituted $C_{1-8}$ alkyl, $C_{3-10}$ cycloalkyl, lower alkyl-$C_{3-10}$ cycloalkyl, alkenyl, aryl, substituted aryl, alkylaryl, or substituted alkylaryl.

2. The process of claim 1, where the acrylate ester is methyl, ethyl or t-butyl acrylate.

3. The process of claim 2, where the base is potassium hydride, sodium hydride, potassium t-butoxide, sodium carbonate, potassium carbonate, cesium carbonate or a teritiary amine, including diisopropylethyl amine, in a polar aprotic solvent such as dimethyl sulfoxide, DMF or acetonitrile.

4. The process of claim 1 where the acrylate ester is t-butyl acrylate, the base is cesium carbonate in DMSO and the mixing temperature is between about 20° C. and about 100° C. such that the compounds produced are represented by formulas 13CPT, 13CPT(R), or 13CPT(S) as described and identified in the specification.

5. The process for producing the compounds described and labeled in the specification as of formula 14G comprising the step of mixing the compounds described and labeled in the specification as of formula 13G with a strong acid; wherein $R_6$ is optionally substituted $C_{1-8}$ alkyl, aryl, substituted aryl, alkylaryl, substituted alkylaryl, $C_{3-10}$ cycloalkyl, lower alkyl-$C_{3-10}$ cycloalkyl, heteroaryl, or substituted heteroaryl; and $R_8$ is optionally substituted $C_{1-8}$ alkyl, $C_{3-10}$ cycloalkyl, lower alkyl-$C_{3-10}$ cycloalkyl, alkenyl, aryl, substituted aryl, alkylaryl, or substituted alkylaryl.

6. The process according to claim 5 where a solvent is added to the mixture.

7. The process according to claim 6 where toluene is the solvent and trifluoroacetic acid is the acid.

8. The process according to claim 5 wherein the compound produced is 14CPT and wherein 14CPT is subsequently reacted with the compounds as described and identified in the specification as U-772 and U-908 to produce an unpurified form of CPT-11.

9. The process according to claim 8 comprising the additional step of purifying the unpurified form of CPT-11 to produce a purified form of CPT-11.

* * * * *